United States Patent
Lietzau et al.

(10) Patent No.: US 7,674,507 B2
(45) Date of Patent: *Mar. 9, 2010

(54) PYRAN-DIOXANE DERIVATIVES, AND THE USE THEREOF IN LIQUID-CRYSTALLINE MEDIA

(75) Inventors: Lars Lietzau, Darmstadt (DE); Markus Czanta, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/915,243

(22) PCT Filed: May 3, 2006

(86) PCT No.: PCT/EP2006/004140

§ 371 (c)(1), (2), (4) Date: Nov. 21, 2007

(87) PCT Pub. No.: WO2006/125511

PCT Pub. Date: Nov. 30, 2006

(65) Prior Publication Data

US 2008/0193682 A1 Aug. 14, 2008

(30) Foreign Application Priority Data

May 25, 2005 (EP) .................... 05011324
Aug. 12, 2005 (EP) .................... 05017654

(51) Int. Cl.
*C09K 19/34* (2006.01)

(52) U.S. Cl. .................... 428/1.1; 252/299.61

(58) Field of Classification Search .................. 428/1.1; 252/299.61, 299.63, 299.66
See application file for complete search history.

(56) References Cited

U.S. PATENT DOCUMENTS

| 4,818,431 A | 4/1989 | Eidenschink et al. |
| 7,445,819 B2 * | 11/2008 | Czanta et al. ................. 428/1.1 |
| 7,482,044 B2 * | 1/2009 | Czanta et al. ................. 428/1.3 |
| 2004/0065866 A1 | 4/2004 | Kato et al. |
| 2006/0058527 A1 | 3/2006 | Kirsch et al. |
| 2006/0278850 A1 * | 12/2006 | Czanta et al. .......... 252/299.61 |
| 2006/0289829 A1 | 12/2006 | Kirsch et al. |
| 2007/0034828 A1 | 2/2007 | Kirsch et al. |
| 2007/0205396 A1 * | 9/2007 | Czanta et al. .......... 252/299.61 |
| 2008/0085380 A1 * | 4/2008 | Wittek et al. ................. 428/1.1 |
| 2008/0124492 A1 * | 5/2008 | Czanta et al. ................. 428/1.1 |

FOREIGN PATENT DOCUMENTS

| DE | 103 18 420 A1 | 11/2004 |
| DE | 10 2004 025 809 A1 | 12/2004 |
| EP | 117 476 A | 9/1984 |
| EP | 1 362 839 A | 11/2003 |
| WO | WO 2004/048357 A1 | 6/2004 |
| WO | WO 2004/106459 A | 12/2004 |

* cited by examiner

*Primary Examiner*—Shean C Wu
(74) *Attorney, Agent, or Firm*—Millen, White, Zelano, Branigan, P.C.

(57) ABSTRACT

The invention relates to pyran-dioxane derivatives and to the use thereof as component(s) in liquid-crystalline media. In addition, the present invention relates to liquid-crystal and electro-optical display elements which contain the liquid-crystalline media according to the invention.

11 Claims, No Drawings

PYRAN-DIOXANE DERIVATIVES, AND THE USE THEREOF IN LIQUID-CRYSTALLINE MEDIA

The invention relates to pyran-dioxane derivatives and to the use thereof as component(s) in liquid-crystalline media. In addition, the present invention relates to liquid-crystal and electro-optical display elements which contain the liquid-crystalline media according to the invention.

In past years, the areas of application of liquid-crystalline compounds have been considerably broadened to various types of display devices, electro-optical equipment, electronic components, sensors, etc. For this reason, a number of different structures have been proposed, in particular in the area of nematic liquid crystals, which have to date found the broadest use in liquid-crystalline display devices. In particular, passive TN or STN matrix displays or systems comprising a TFT active matrix have been employed.

The liquid-crystalline compounds according to the invention can be used as component(s) of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering.

The use of certain tetrahydropyran derivatives as liquid-crystalline substances is known.

DE 102004025808 A1 discloses the synthesis of a compound which consists of 3 rings, where one tetrahydropyran ring and one dioxane ring is present in each case. The substances have positive values of the dielectric anisotropy $\Delta\varepsilon$.

In addition, various tetrahydropyran derivatives as liquid-crystalline material and the preparation thereof have already been described, such as, for example, in DE 102004025809 A1, DE 10318420 A1 or WO 2004/048357 A1.

The present invention was based on the object of finding novel stable liquid-crystalline or mesogenic compounds which are suitable as component(s) of liquid-crystalline media. In particular, the compounds should at the same time have comparatively low viscosity and a dielectric anisotropy in the positive region. For many current mixture concepts in the area of liquid crystals, it is advantageous to use compounds having a particularly high dielectric anisotropy $\Delta\varepsilon$.

With respect to the very wide variety of areas of use of such compounds of high $\Delta\varepsilon$, it was desirable to have available further compounds, preferably of high nematogeneity, which have properties which are precisely customised to the particular applications.

One object of the invention was thus to find novel stable liquid-crystalline or mesogenic compounds which are suitable as component(s) of liquid-crystalline media, in particular for TN, STN, IPS and TFT displays.

A further object of the present invention was to provide liquid-crystalline or mesogenic compounds which, alone or in mixtures, have a high dielectric anisotropy Ac, a high clearing point and a low rotational viscosity $\gamma_1$. In addition, the compounds according to the invention should be thermally and photochemically stable. Furthermore, the compounds according to the invention should have the broadest possible nematic phase. As mesogens, they should facilitate a broad nematic phase in mixtures with liquid-crystalline co-components and be extremely miscible with nematic base mixtures, in particular at low temperatures.

Surprisingly, it has been found that the pyran-dioxane derivatives according to the invention are eminently suitable as components of liquid-crystalline media. They can be used to obtain stable liquid-crystalline media, suitable in particular for TN-TFT and STN displays, but also for IPS systems or more recent concepts which require particularly high dielectric anisotropies. The compounds according to the invention are both thermally and UV-stable. They are also distinguished by strongly positive dielectric anisotropies $\Delta\varepsilon$, due to which relatively low threshold voltages are necessary in the application in optical switching elements.

Particularly high values are also achieved, in particular, by the quotient $\Delta\varepsilon/\Delta n$ of the compounds according to the invention, i.e. for the same values of $\Delta\varepsilon$, relatively low values of the optical anisotropy $\Delta n$ are facilitated by the substances according to the invention. In addition, the compounds according to the invention have a high clearing point and at the same time favourable values for the rotational viscosity.

The provision of the pyran-dioxane derivatives according to the invention very generally considerably broadens the range of liquid-crystalline substances which are suitable, from various applicational points of view, for the preparation of liquid-crystalline mixtures.

The pyran-dioxane derivatives according to the invention have a broad range of applications. Depending on the choice of substituents, these compounds can serve as base materials of which liquid-crystalline media are predominantly composed. However, it is also possible to add liquid-crystalline base materials from other classes of compound to the compounds according to the invention in order, for example, to modify the dielectric and/or optical anisotropy of a dielectric of this type and/or to optimise its threshold voltage and/or its viscosity.

In the pure state, the pyran-dioxane derivatives according to the invention are colourless. They are stable thermally and to light.

The present invention thus relates to pyran-dioxane derivatives of the general formula I

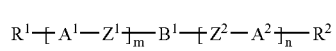

in which

B¹

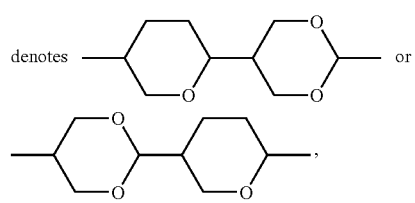

denotes ——⟨⟩——⟨⟩—— or ——⟨⟩——⟨⟩——,

R¹, R² denote H, halogen, CN, SCN, NCS, SF₅, a linear or branched, optionally chiral alkyl radical having 1 to 15 C atoms which is unsubstituted, monosubstituted by CN or CF₃ or mono- or polysubstituted by halogen and in which one or more $CH_2$ groups may each be replaced, independently of one another, by —O—, —S—, —CO—, —CO—O—, —O—CO—, —CH=CH—, —CH=CF—, —CF=CF—, —C≡C—, —CH₂O— or —CF₂O— in such a way that heteroatoms are not linked directly to one another and asymmetrical groups may be present in both orientations, A¹, A² each, independently of one another, identically or differently, denote a) trans-1,4-cyclohexylene, in which, in addition, one or more non-adjacent CH₂ groups may be replaced by —O— and/or —S—,
b) 1,4-phenylene, in which one or two CH groups may be replaced by N and in which one or more H atoms may be replaced by Br, Cl, F, CN, methyl, methoxy or a mono- or polyfluorinated methyl or methoxy group,
c) a radical from the group 1,4-bicyclo[2.2.2]octylene, piperidine-1,4-diyl, cyclobutane-1,3-diyl, spiro[3.3]heptane-2,6-diyl,

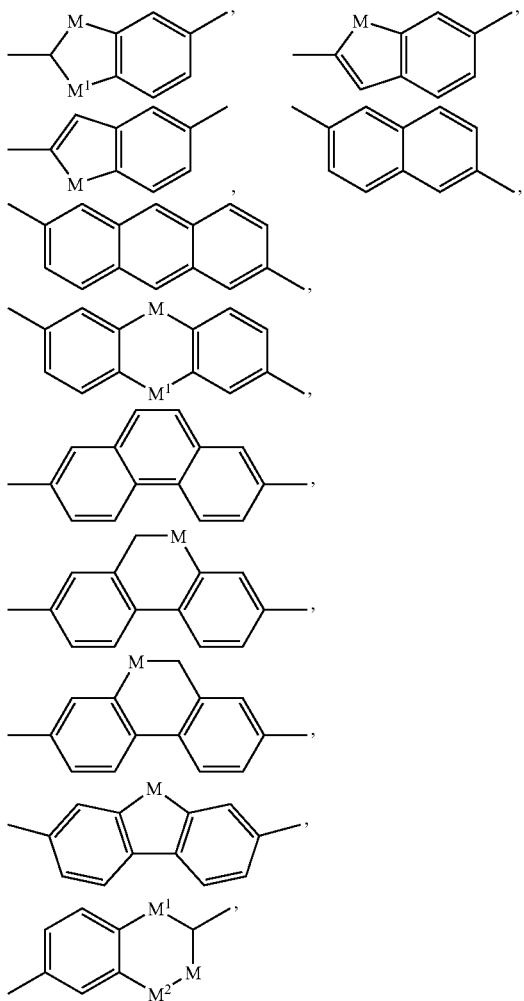

in which hydrogen atoms may be mono- or polysubstituted by F, CN, SCN, SF₅, CH₂F, CHF₂ or CF₃, OCH₂F, OCHF₂ or OCF₃,
one or more double bonds may be replaced by single bonds,
M, M¹ or M² denotes —O—, —S—, —CH₂—, —CHY— or —CYY¹—, and
Y and Y¹ denote Cl, F, CN, OCF₃ or CF₃, or
d) 1,4-cyclohexenylene,
Z¹, Z² each, independently of one another, identically or differently, denote a single bond, —CH₂O—, —CO—O—, —CF₂O—, —CH₂CH₂CF₂O—, —CF₂CF₂—, —CH₂CF₂—, —CH₂CH₂—, —CH=CH—, —CH=CF—, —CF=CF— or —C≡C—, where asymmetrical bridges may be oriented to both sides, and n, m, independently of one another, denote 0, 1, 2 or 3, with the proviso that if m=0, n=1 and at the same time A² denotes a phenylene as in b), then Z², in the stated orientation, denotes

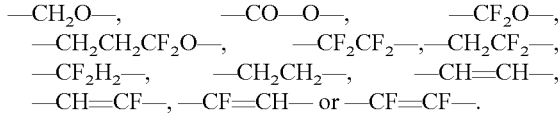

n+m is preferably 1, 2, 3 or 4, particularly preferably 1, 2 or 3 and very particularly preferably 2 or 3.

The present invention furthermore relates to the use of compounds of the formula I as component(s) in liquid-crystalline media.

The present invention likewise relates to liquid-crystalline media having at least two liquid-crystalline components which comprise at least one pyran-dioxane derivative of the formula I.

The present invention also relates to liquid-crystal display elements, in particular electro-optical display elements, which contain, as dielectric, a liquid-crystalline medium according to the invention.

The meaning of the formula I encompasses all isotopes of the chemical elements bonded in the compounds of the formula I. In enantiomerically pure or enriched form, the compounds of the formula I are in principle also suitable as chiral dopants and in general for achieving chiral mesophases.

Above and below, $R^1$, $R^2$, $A^1$, $A^2$, $Z^1$, $Z^2$, n and m have the meanings indicated, unless expressly stated otherwise. If the radicals $A^1$, $A^2$, $Z^1$ and $Z^2$ occur more than once between surrounding brackets, they can, independently of one another, adopt identical or different meanings. If the ring $A^1$ or $A^2$ is present twice, the two rings may have identical or different meanings. The corresponding situation applies to 3 rings. The same also applies to the bridges $Z^1$ and $Z^2$.

Preferred embodiments of the compounds of the general formula I according to the invention are described below:

In a preferred embodiment, the compounds of the formula I are characterised in that n+m is greater than or equal to 2 and very particularly 2 or 3.

Particular preference is given here to compounds of the formula I in which n is equal to 2 and m is equal to 0 or 1.

Preference is likewise given to compounds of the formula I which are characterised in that n denotes 1, 2 or 3, and at least one Z² denotes

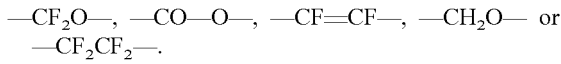

Of the possible rings $A^1$ and $A^2$ in formula I, preference is given to rings in accordance with definitions a) and b) and furthermore rings from groups d) and carbocyclic bicyclic systems from c), such as, for example, indanes.

Of the possible groups $Z^1$ and $Z^2$, preference is given to the groups —CF₂O—, —OCF₂—, —CF₂CF₂—, —CF=CF— or the single bond. The single bond is very particularly preferred.

Preference is given to compounds of the formula IA

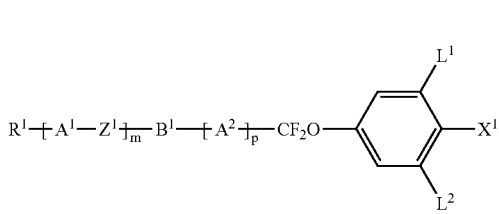

in which
L¹ L², independently of one another, denote H, F, Cl, CN or CF₃,
p denotes 0, 1 or 2, preferably 0 or 1,
m+p denotes 0, 1 or 2, preferably 0 or 1, and
$X^1$ denotes H, halogen, CN, SCN, NCS, SF₅, a linear or branched alkyl radical having 1 to 8 C atoms which is monosubstituted by CN or CF₃ or at least monosubstituted by halogen and in which one or more CH₂ groups may each, independently of one another, be replaced by —O—, —CF=CF— or —C≡C— in such a way that heteroatoms are not linked directly to one another, i.e. also, for example, OCF₃ or —CF=CF₂, and the other variables are as defined above for formula I.
In the formulae I and IA, $Z^1$ preferably denotes —CH₂CH₂—, —CH=CH—, —C≡C—, —CF₂CF₂—, —CF=CF—, —CO—O—, —O—CO—, —CF₂O—, —OCF₂— or a single bond, particularly preferably —CF₂O—, —CF₂CF₂— or a single bond. In the case where m is >1, at least one of the $Z^1$ preferably denotes a single bond.

Very particular preference is given to compounds of the formula IB

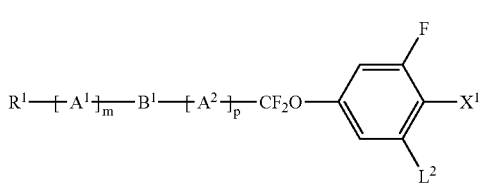

in which
$L^2$ denotes H or F,
$X^1$ denotes F or OCF₃, CF₃, CN, NCS, SCN, SF₅,
$A^1$ denotes a 1,4-cyclohexanediyl,
$A^2$ denotes a group of the formula

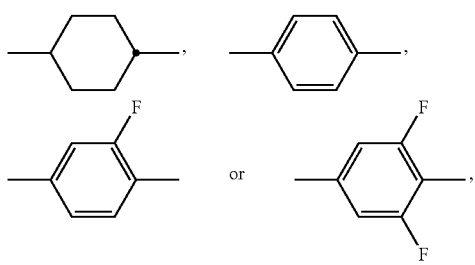

m denotes 0 or 1,
p denotes 0 or 1, preferably 1, and
m+p denotes 0 or 1, preferably 1.

Preference is in each case given to compounds of the formulae I, IA and IB in which $R^1$ denotes a linear alkyl or alkoxy radical having 1 to 12 C atoms or a linear alkenyl or alkenyloxy radical having 2 to 12 C atoms.

Particular preference is also given to the compounds of the formulae IA and IB in which $L^2$ stands for fluorine. Particular preference is also given to the compounds of the formulae IA and IB in which $X^1$ stands for fluorine or OCF₃.

The very particularly preferred compounds according to the invention are accordingly I-1 to I-4:

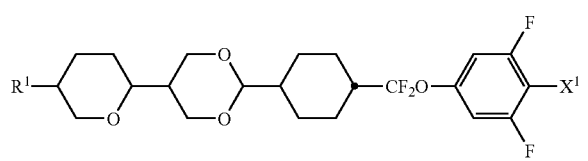

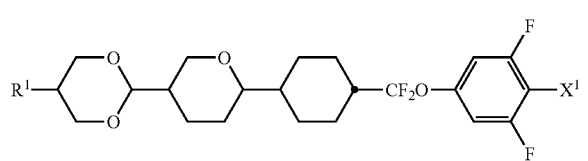

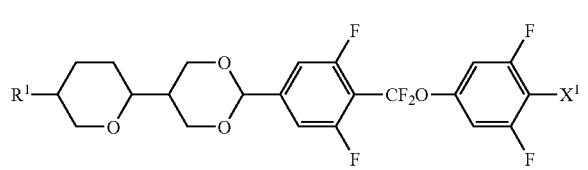

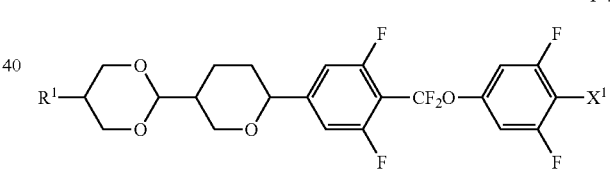

where $X^1$ and $R^1$ are as defined for IB, and where $R^1$ preferably denotes a linear alkyl or alkoxy radical having 1 to 10 C atoms or a linear alkenyl or alkenyloxy radical having 2 to 10 C atoms. $X^1$ preferably denotes F or OCF₃.

In the above preferred formulae, $R^1$ preferably denotes a linear alkyl or alkoxy radical having 1 to 7 C atoms or a linear alkenyl or alkenyloxy radical having 2 to 7 C atoms, in which a —CH₂— group may be replaced by —O— in such a way that two adjacent groups are not replaced by —O—. $R^1$ particularly preferably denotes a linear alkyl radical or alkoxy radical having 1 to 7 C atoms or a linear alkenyl radical having 2 to 7 C atoms.

If $R^1$ or $R^2$ in the formulae above and below denotes an alkyl radical, this may be straight-chain or branched. It is particularly preferably straight-chain, has 1, 2, 3, 4, 5, 6 or 7 C atoms and accordingly denotes methyl, ethyl, propyl, butyl, pentyl, hexyl or heptyl, furthermore octyl, nonyl, decyl, undecyl, dodecyl, tridecyl, tetradecyl or pentadecyl.

If $R^1$ or $R^2$ denotes an alkyl radical in which one CH₂ group has been replaced by —O—, this may be straight-chain or branched. It is preferably straight-chain and has 1 to 10 C atoms. The first CH$_2$ group in this alkyl radical has particularly preferably been replaced by —O—, so that the radical R$^1$ acquires the meaning alkoxy and denotes methoxy, ethoxy, propoxy, butoxy, pentyloxy, hexyloxy, heptyloxy, octyloxy or nonyloxy.

Furthermore, a CH$_2$ group elsewhere may also have been replaced by —O—, so that the radical R$^1$ and/or R$^2$ preferably denotes straight-chain 2-oxa-propyl (=methoxymethyl), 2-(=ethoxymethyl) or 3-oxabutyl (=2-methoxy-ethyl), 2, 3- or 4-oxapentyl, 2-, 3-, 4- or 5-oxahexyl, 2-, 3-, 4-, 5- or 6-oxa-heptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R$^1$ or R$^2$ denotes an alkyl radical in which one CH$_2$ group has been replaced by —CH=CH—, this may be straight-chain or branched. It is preferably straight-chain and has 2 to 10 C atoms. Accordingly, it denotes vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1 -, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Preferred alkenyl groups are C$_2$-C$_7$-1 E-alkenyl, C$_4$-C$_7$-3E-alkenyl, C$_5$-C$_7$-4-alkenyl, C$_6$-C$_7$-5-alkenyl and C$_7$-6-alkenyl, particularly preferably C$_2$-C$_7$-1E-alkenyl, C$_4$-C$_7$-3E-alkenyl and C$_5$-C$_7$-4-alkenyl.

Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl and 6-heptenyl. Groups having up to 5 carbon atoms are particularly preferred.

If R$^1$ or R$^2$ denotes an alkyl radical in which one CH$_2$ group has been replaced by —o— and one has been replaced by —CO—, these are preferably adjacent. These thus contain an acyloxy group —CO—O— or an oxycarbonyl group —O—CO—. These are particularly preferably straight-chain and have 2 to 6 C atoms.

Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)-propyl, 3-(ethoxycarbonyl)propyl or 4-(methoxycarbonyl)butyl.

If R$^1$ or R$^2$ denotes an alkyl radical in which one CH$_2$ group has been replaced by unsubstituted or substituted —CH=CH— and an adjacent CH$_2$ group has been replaced by —CO—, —CO—O— or —O—CO—, this may be straight-chain or branched. It is preferably straight-chain and has 4 to 13 C atoms. Accordingly, it particularly preferably denotes acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxy-nonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R$^1$ or R$^2$ denotes an alkyl or alkenyl radical which is monosubstituted by CN or CF$_3$, this radical is preferably straight-chain and the substitution by CN or CF$_3$ is in the ω-position.

If R$^1$ or R$^2$ denotes an alkyl or alkenyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent may be in any desired position, but preferably in the ω-position.

Compounds of the formula I having a branched wing group R$^1$ may occasionally be of importance owing to better solubility in the conventional liquid-crystalline base materials, but in particular as chiral dopants if they are optically active. Smectic compounds of this type are suitable as component(s) of ferroelectric materials.

Branched groups of this type preferably contain not more than one chain branch. Preferred branched radicals R$^1$ are isopropyl, 2-butyl (=1-methyl-propyl), isobutyl (=2-methyl-propyl), 2-methylbutyl, isopentyl (=3-methyl-butyl), 2-methylpentyl, 3-methylpentyl, 2-ethylhexyl, 2-propylpentyl, isopropoxy, 2-methylpropoxy, 2-methylbutoxy, 3-methylbutoxy, 2-methyl-pentyloxy, 3-methylpentyloxy, 2-ethylhexyloxy, 1-methylhexyloxy and 1-methylheptyloxy.

For certain applications of the compounds according to the invention, for example in order to achieve particularly low viscosities, it is advantageous that the sequence of the rings in the structural element B$^1$ is pyran-dioxane (corresponding to the images). Position 2 of the tetrahydropyran ring here is linked to position 5 of the dioxane ring.

The formula I and the sub-formulae IA, IB and IC usually encompass, in the case of chiral compounds, the racemates of these compounds, but also both optically pure components per se, as well as enriched mixtures of these components.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

The dioxane ring in the compounds is generally prepared by condensation of an aldehyde with a 2-substituted 1,3-diol. The tetrahydropyran ring, which is either attached to the diol or to the aldehyde group here, is prepared by one of the numerous known processes for the synthesis of 2,5-disubstituted tetrahydropyrans. There are a number of synthetic routes for the tetrahydropyran-2-aldehydes: by reduction of a corresponding carboxylic acid derivative, by mild oxidation of a corresponding alcohol (carbinol) or by catalytic hydroformylation of a suitable dihydropyran.

The starting materials for the above process are either known or can be prepared analogously to known compounds.

If desired, the starting materials can also be formed in situ by not isolating them from the reaction mixture, but instead immediately converting them further into the compounds of the formula I.

The reactions depicted should only be regarded as illustrative. The person skilled in the art will be able to carry out corresponding variants of the syntheses presented and also follow other suitable synthetic routes in order to obtain the compounds of the formula I according to the invention.

The synthesis of various derivatives of the general formula I is, in addition, described in detail in the examples. The synthetic methods can be varied, enabling all compounds according to the invention to be prepared with the aid of modified starting materials.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

R'-L-E-R''  (1)

R'-L-COO-E-R''  (2)

R'-L-OOC-E-R''  (3)

R'-L-CH$_2$CH$_2$-E-R''  (4)

R'-L-C≡C-E-R''  (5)

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Py-, -G-Phe- and -G-Cyc- and their mirror images, where Phe denotes unsubstituted or fluorine-substituted 1,4-phenylene, Cyc denotes trans-1,4-cyclo-hexylene or 1,4-cyclohexenylene, Pyr denotes pyrimidine-2,5-diyl or pyridine-2,5-diyl, Dio denotes 1,3-dioxane-2,5-diyl, Py denotes tetrahydropyran-2,5-diyl and G denotes 2-(trans-1,4-cyclohexyl) ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe, Py and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R'' each, independently of one another, denote alkyl, alkenyl, alkoxy, alkoxyalkyl, alkenyloxy or alkanoyloxy having up to 8 C atoms, —F, —Cl, —CN, —NCS, —(O)$_i$CH$_{3-(k+I)}$F$_k$Cl$_I$, where i is 0 or 1, k and I, independently of one another, identically or differently, are 0, 1, 2 or 3, but with the proviso that the sum (k+I) is 1, 2 or 3.

In a smaller sub-group of the compounds of the formulae 1, 2, 3, 4 and 5, R' and R'' each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R'' are different from one another, one of these radicals usually being alkyl, alkenyl, alkoxy or alkoxyalkyl.

In another smaller sub-group of the compounds of the formulae 1, 2, 3, 4 and 5, which is referred to as group B, R'' denotes —F, —Cl, —NCS or —(O)$_i$CH$_{3-(k+I)}$F$_k$Cl$_I$, where i is 0 or 1, k and I, independently of one another, are 0, 1, 2 or 3, but with the proviso that the sum (k+I) is 1, 2 or 3. The compounds in which R'' has this meaning are referred to by the sub-formulae 1b, 2b, 3b, 4b and 5b. Particular preference is given to those compounds of the sub-formulae 1b, 2b, 3b, 4b and 5b in which R'' has the meaning —F, —Cl, —NCS, —CF$_3$, —OCHF$_2$ or —OCF$_3$.

In the compounds of the sub-formulae 1b, 2b, 3b, 4b and 5b, R' has the meanings indicated in the case of the compounds of the sub-formulae 1a to 5a and is preferably alkyl, alkenyl, alkoxy or alkoxyalkyl.

In a further smaller sub-group of the compounds of the formulae 1, 2, 3, 4 and 5, R'' denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

group A: 0 to 90%, preferably 20 to 90%, particularly preferably 30 to 90%;

group B: 0 to 80%, preferably 10 to 80%, particularly preferably 10 to 65%;

group C: 0 to 80%, preferably 5 to 80%, particularly preferably 5 to 50%;

where the sum of the proportions by weight of the group A, B and/or C compounds present in the respective media according to the invention is preferably 5 to 90% and particularly preferably 10 to 90%.

The media according to the invention preferably comprise 1 to 40%, particularly preferably 5 to 30%, of the compounds according to the invention. Preference is furthermore given to media comprising more than 40%, particularly preferably 45 to 90%, of compounds according to the invention. The media preferably comprise three, four or five compounds according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0 to 15%, preferably 0 to 10%, of pleochroic dyes and/or chiral dopants can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are indicated without taking into account the concentration of these additives.

The following examples explain the invention without being intended to restrict it.

Above and below, the following abbreviations are used:

| | |
|---|---|
| RT | room temperature |
| THF | tetrahydrofuran |
| MTB ether | methyl tert-butyl ether |
| LAH | lithium aluminium hydride |
| p-TsOH | p-toluenesulfonic acid |
| TLC | thin-layer chromatography |
| DBN | 1,5-diazabicyclo[4.3.0]non-5-ene |
| DMSO | dimethyl sulfoxide |
| DMF | dimethylformamide |
| BuLi | n-butyllithium |

In addition, the following abbreviations are used: C: crystalline phase; N: nematic phase; I: isotropic phase, Sm: smectic phase. The numbers between the abbreviations for the phases correspond to the transition temperatures for the pure substance. The first transition temperature starting from the crystalline phase (C) corresponds to the melting point.

Temperature data are in ° C., unless indicated otherwise.
In addition, clp. denotes clearing point and $\gamma_1$ denotes rotational viscosity. Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt. The dielectric anisotropy $\Delta\epsilon$ is determined at 1 kHz. The optical anisotropy $\Delta n$ is determined at a wavelength of 589.3 nm. All measurement values are determined at a temperature of 20° C., unless indicated otherwise. For clp., $\Delta\epsilon$, $\Delta n$ and $\gamma_1$, 10% by weight of the substance to be investigated are measured dissolved in the dielectrically posi-tive mixture ZLI-4792 (Merck KGaA), and the measurement value is extrapolated to a content of 100%.

EXAMPLE 1

EXAMPLE 1.a

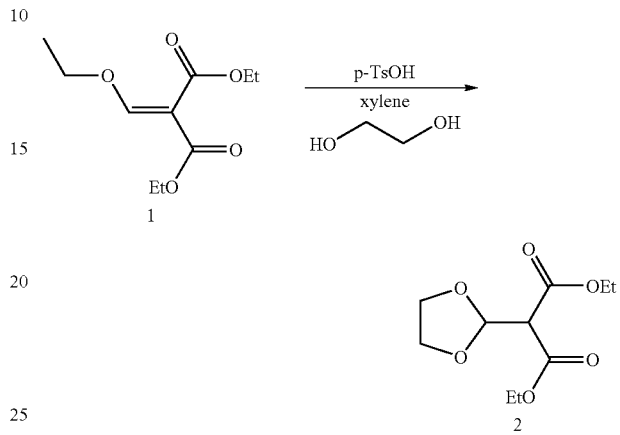

375 ml (1.87 mol) of the malonate 1 are dissolved in 2.1 l of xylene with 142 ml (2.55 mol) of ethylene glycol and 9.75 g (50 mmol) of p-toluene-sulfonic acid monohydrate, and the mixture is heated to the boil. In the process, 1 l of xylene is distilled off at a top temperature of 140° C. The mixture remaining in the flask is washed with sodium hydrogencarbonate and evaporated. The resultant residue, consisting of 2, is subjected to fractional distillation under reduced pressure. Yield: 280 g of a colourless liquid.

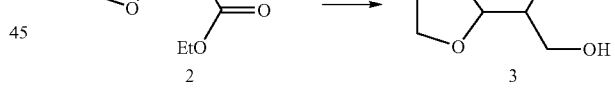

A solution of 187.2 g (790 mmol) of the malonate 2 in THF is added under nitrogen to a suspension of 45.5 g (1.03 mol) of lithium aluminium hydride in 1 l of THF at the boiling temperature, and the mixture is heated at the boil for 1 h. The cooled batch is hydrolysed using a THF/water mixture (4:1), and a solution of sodium carbonate decahydrate in 123 ml of water at 80° C. is added. After 230 min, the resultant solid 3 is separated off and washed with MTB ether. The organic phase is evaporated and employed without further purification in the following step.

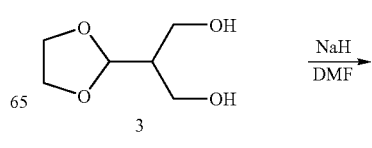

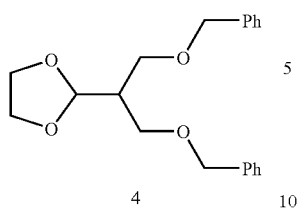

86.3 g (580 mmol) of the diol 3 are dissolved in 1100 ml of DMF under nitrogen, and 14 g (38 mmol) of tetra-n-butylammonium iodide are added. 87.2 g (2.18 mol) of a 60% sodium hydride suspension in mineral oil are subsequently introduced in portions. After 30 min at RT, 264 ml (2.18 mol) of benzyl bromide are carefully added with cooling. After 48 h at RT, the batch is added to 3 l of water and extracted with MTB ether. The organic phase is washed with water and evaporated. The residue is passed over silica gel (toluene). 3 fractions of 4 are isolated.

69.6 g; content 62.9%
194.1 g; content 92.1 %
23.0 g; content 64.8%

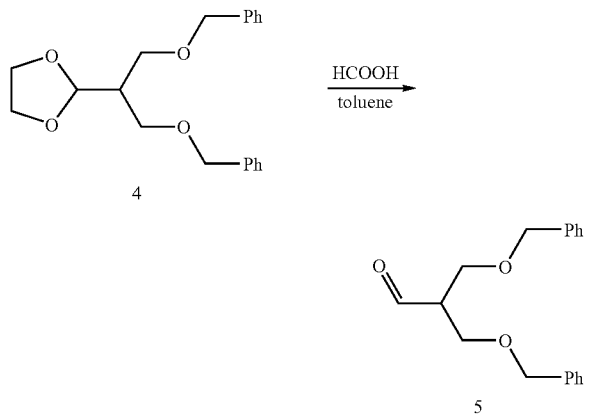

290 ml of formic acid are added to a solution of 194 g (92.1%; 540 mmol) of the acetal 4 in 830 ml of toluene, and the mixture is held at 60° C. for 6 h with vigorous stirring. 1 l of heptane and 1 l of water are added to the cooled batch. The organic phase is washed with water and sodium hydrogencarbonate solution and evaporated. The residue is passed over silica gel (toluene/heptane). 163.7 g of the aldehyde 5 are isolated.

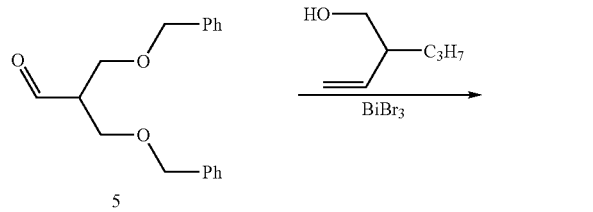

22.5 g (63%; 50 mmol) of the aldehyde 5 and 5.95 g (96%; 50 mmol) of 2-vinylpropanol are dissolved in 140 ml of dichloromethane, and 11.4 g (25 mmol) of bismuth(III) bromide are added. The batch is stirred overnight at RT. The batch is subsequently filtered through silica gel and evaporated. 26.1 g of the bromine compound 6 are isolated.

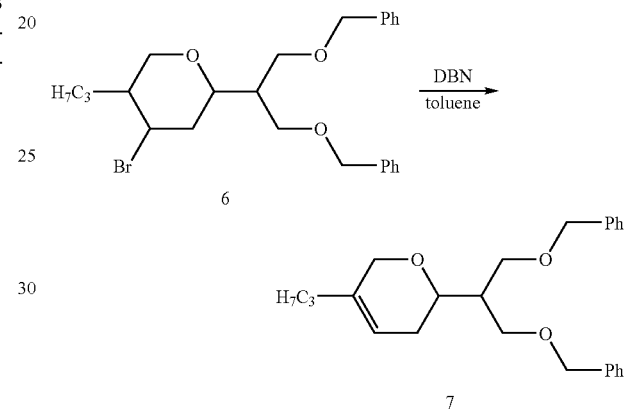

100 g (219 mmol) of the bromine compound 6 are dissolved in 165 ml of toluene under nitrogen, 38.5 ml of DBN are added, and the mixture is 25 heated at the boil for 5 h. 200 ml of water are subsequently added to the cooled batch, and the mixture is acidified using dilute sulfuric acid. The organic phase is diluted with 300 ml of heptane, separated off, washed with sodium hydrogencarbonate solution and evaporated. The resultant residue is passed over silica gel (toluene). 57.1 g of the compound 7 are isolated.

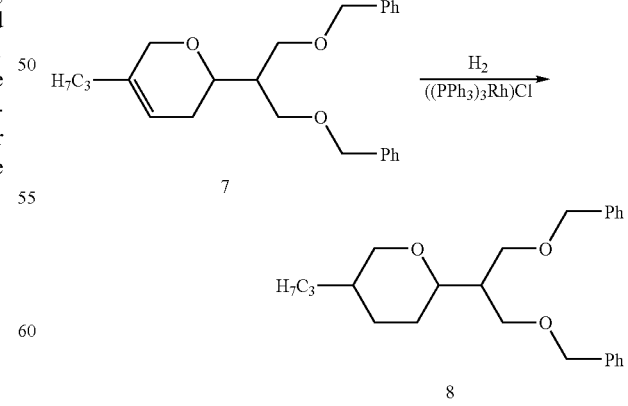

57 g (150 mmol) of the unsaturated pyran 7 are dissolved in 360 ml of methanol and 90 ml of toluene and hydrogenated at 8 bar/80° C. on a (PPh$_3$)$_3$RhCl catalyst. The hydrogenation solution is evaporated, and the residue is passed over silica gel (toluene/MTB ether), giving two fractions of the pyran 8: 32.1 g and 21.6 g.

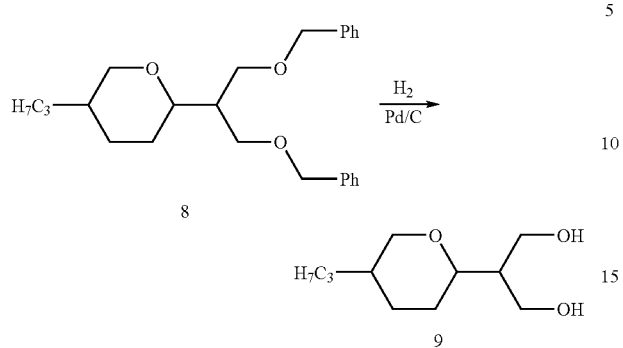

32.1 g (77%) of the protected diol 8 are dissolved in 321 ml of THF and hydrogenated on a palladium catalyst. The catalyst is subsequently separated off, and the solution is evaporated. The resultant residue of 9 is employed without further purification in the following step.

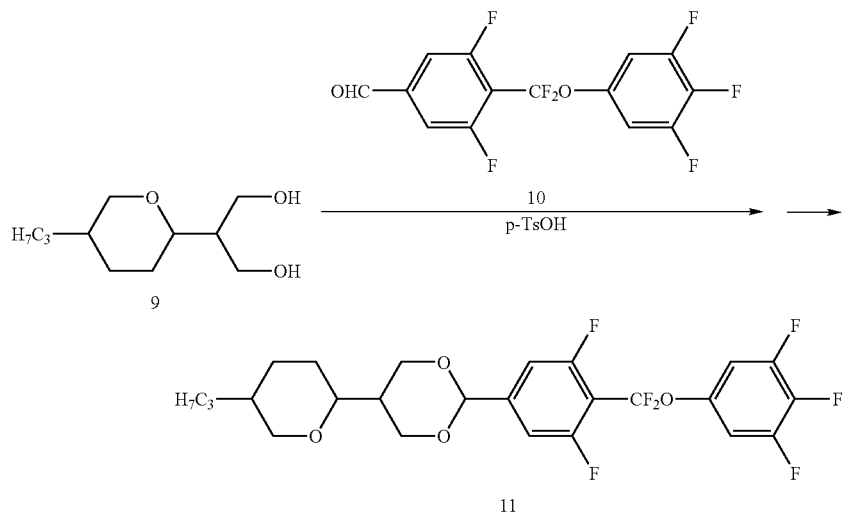

15.8 g (78 mmol) of the diol 9 are dissolved in 100 ml of toluene with 27.4 g (78 mmol) of the aldehyde 10, 500 mg of p-toluenesulfonic acid monohydrate are added, and the mixture is heated to the boil on a water separator. The batch is subsequently passed over silica gel, and the eluate is evaporated. The resultant residue of 11 is purified by crystallisation from acetonitrile, acetone and heptane.

EXAMPLE 1. b

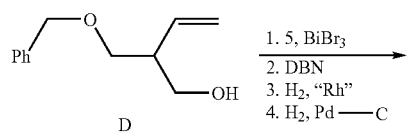

-continued

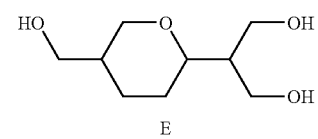

A compound analogous to Example 1. a with a double bond in the terminal side chain can be prepared via the homoallyl alcohol D, which is prepared as described by J. N. Zonjee et al., *Tetrahedron* 1989, 45, 7553-7567. To this end, the compound D is reacted analogously to Example 1. a successively with 5 to give the bromopyran, then with DBU in toluene and subsequent hydrogenation (after removal of all protecting groups, see reaction 8→9) to give compound E.

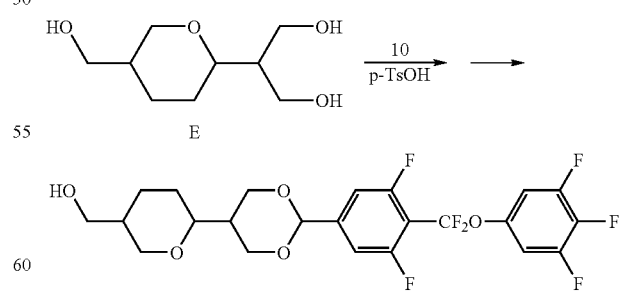

The ring closure of the trihydroxy compound E to give the dioxane F is carried out by condensation with the aldehyde 10 analogously to reaction 9→11.

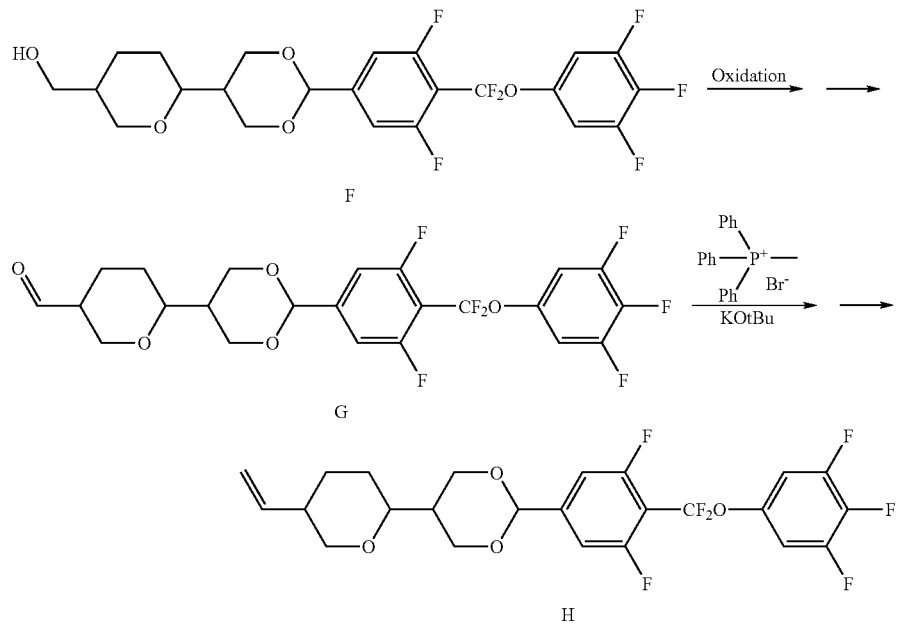

In the further synthesis, the remaining OH function in formula F is oxidised to the aldehyde by the method of Swern using NaOAc/PCC or by the method of Dess-Martin using periodinane, and converted into a double bond via a Wittig reaction (H). Depending on the Wittig salt, the position of the double bond can be varied (via a plurality of reaction steps) or disubstituted. It is also possible to introduce a plurality of double bonds.

The following compounds are prepared from in each case a diol analogous to compound 9 and a suitable aldehyde analogous to 10:

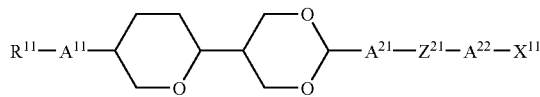

where $R^{11}, A^{11}, A^{21}, Z^{21}, A^{22}$ and $X^{11}$ denote, in particular, in accordance with Table 1:

TABLE 1

| Compounds for Example 1. | | | | | | | |
|---|---|---|---|---|---|---|---|
| # | $R^{11}$ | $A^{11}$ | $A^{21}$ | $Z^{21}$ | $A^{22}$ | $X^{11}$ | Values |
| 1 | $CH_3$ | — | ![2,6-difluorophenyl] | —$CF_2O$— | ![2,6-difluorophenyl] | F | |
| 2 | $C_2H_5$ | — | ![2,6-difluorophenyl] | —$CF_2O$— | ![2,6-difluorophenyl] | F | C 93 N (84) I; Clp. = 79 Δε = 33.5 Δn = 0.091 $\gamma_1$ = 192 |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 3 | $C_3H_7$ | — | 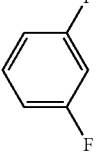 | —$CF_2O$— | 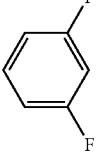 | F | C 92 N 113 I; Clp. = 97; $\Delta\epsilon$ = 35; $\Delta n$ = 0.099; $\gamma_1$ = 320 |
| 4 | $C_4H_9$ | — | 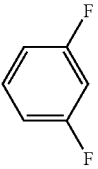 | —$CF_2O$— | 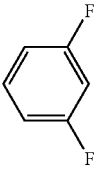 | F | C 88 N 108 I; Clp. = 97; $\Delta\epsilon$ = 31; $\Delta n$ = 0.093 |
| 5 | $C_5H_{11}$ | — | 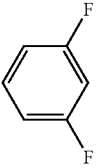 | —$CF_2O$— | 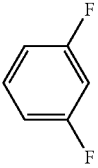 | F | C 86 N 112 I; Clp. = 104; $\Delta\epsilon$ = 31; $\Delta n$ = 0.094; $\gamma_1$ = 354 |
| 6 | $CH_3$ | — | 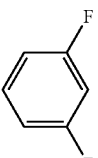 | —$CF_2O$— | 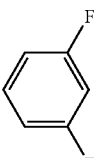 | $OCF_3$ | |
| 7 | $C_2H_5$ | — | 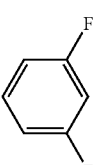 | —$CF_2O$— | 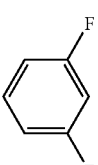 | $OCF_3$ | C 107 SmA (89) N (120) I; $\Delta\epsilon$ = 34; $\Delta n$ = 0.097 |
| 8 | $C_3H_7$ | — | 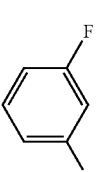 | —$CF_2O$— | 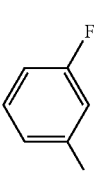 | $OCF_3$ | C 101 SmA 108 N 135 I; $\Delta\epsilon$ = 34; $\Delta n$ = 0.098 |
| 9 | $C_4H_9$ | — | 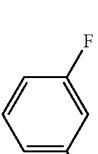 | —$CF_2O$— | 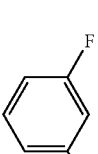 | $OCF_3$ | C 103 SmA 112 N 132 I; Clp. = 103; $\Delta\epsilon$ = 34; $\Delta n$ = 0.091 |
| 10 | $C_5H_{11}$ | — | 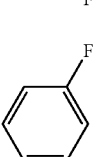 | —$CF_2O$— | 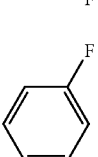 | $OCF_3$ | C 97 SmA 115 N 134 I; Clp. = 110; $\Delta\epsilon$ = 34; $\Delta n$ = 0.093 |

TABLE 1-continued

Compounds for Example 1.

| # | R¹¹ | A¹¹ | A²¹ | Z²¹ | A²² | X¹¹ | Values |
|---|---|---|---|---|---|---|---|
| 11 | $CH_3$ | — | 2,3-difluoro-1,4-phenylene | $-CF_2O-$ | 2,3-difluoro-1,4-phenylene | $CF_3$ | |
| 12 | $C_2H_5$ | — | 2,3-difluoro-1,4-phenylene | $-CF_2O-$ | 2,3-difluoro-1,4-phenylene | $CF_3$ | |
| 13 | $C_3H_7$ | — | 2,3-difluoro-1,4-phenylene | $-CF_2O-$ | 2,3-difluoro-1,4-phenylene | $CF_3$ | C 111 N (99) I; Clp. = 81 $\Delta\epsilon = 45$ $\Delta n = 0.098$ |
| 14 | $C_4H_9$ | — | 2,3-difluoro-1,4-phenylene | $-CF_2O-$ | 2,3-difluoro-1,4-phenylene | $CF_3$ | |
| 15 | $C_5H_{11}$ | — | 2,3-difluoro-1,4-phenylene | $-CF_2O-$ | 2,3-difluoro-1,4-phenylene | $CF_3$ | |
| 16 | $CH_3$ | — | 2,3-difluoro-1,4-phenylene | $-CF_2O-$ | 3-fluoro-1,4-phenylene | F | |
| 17 | $C_2H_5$ | — | 2,3-difluoro-1,4-phenylene | $-CF_2O-$ | 3-fluoro-1,4-phenylene | F | |
| 18 | $C_3H_7$ | — | 2,3-difluoro-1,4-phenylene | $-CF_2O-$ | 3-fluoro-1,4-phenylene | F | |

TABLE 1-continued
Compounds for Example 1.
| # | R$^{11}$ | A$^{11}$ | A$^{21}$ | Z$^{21}$ | A$^{22}$ | X$^{11}$ | Values |
|---|---|---|---|---|---|---|---|
| 19 | C$_4$H$_9$ | — | 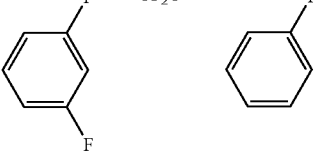 | —CF$_2$O— | 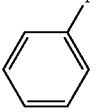 | F | |
| 20 | C$_5$H$_{11}$ | — | 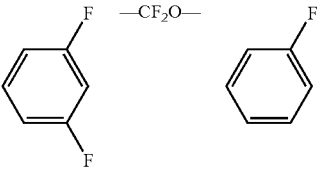 | —CF$_2$O— | 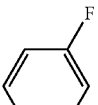 | F | |
| 21 | CH$_3$ | — | 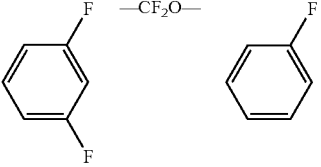 | —CF$_2$O— | 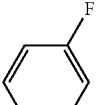 | OCF$_3$ | |
| 22 | C$_2$H$_5$ | — | 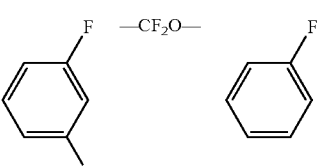 | —CF$_2$O— | 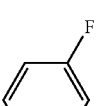 | OCF$_3$ | C 95 SmA 105 N 124 I Clp. = 105 Δε = 30 Δn = 0.096 |
| 23 | C$_3$H$_7$ | — | 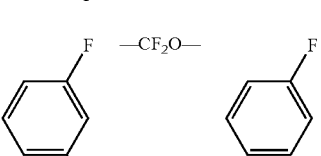 | —CF$_2$O— | 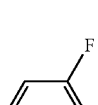 | OCF$_3$ | C 91 SmA 130 N 147 I Clp. = 124 Δε = 28 Δn = 0.105 |
| 24 | C$_4$H$_9$ | — | 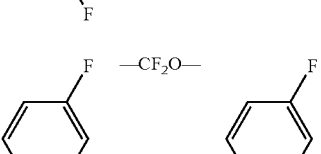 | —CF$_2$O— | 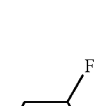 | OCF$_3$ | C 90 SmA 136 N 145 Clp. = 122 Δε = 27 Δn = 0.100 γ$_1$ = 543 |
| 25 | C$_5$H$_{11}$ | — | 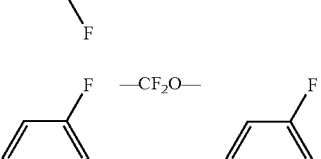 | —CF$_2$O— | 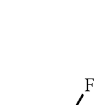 | OCF$_3$ | C 86 SmA 141 N 148 I Clp. = 127 Δε = 26 Δn = 0.103 γ$_1$ = 633 |
| 26 | CH$_3$ | — | 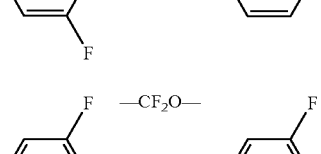 | —CF$_2$O— | 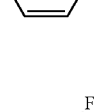 | CF$_3$ | |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 27 | $C_2H_5$ | — | 2,3-difluorophenyl | —CF$_2$O— | 2-fluorophenyl | $CF_3$ | |
| 28 | $C_3H_7$ | — | 2,3-difluorophenyl | —CF$_2$O— | 2-fluorophenyl | $CF_3$ | |
| 29 | $C_4H_9$ | — | 2,3-difluorophenyl | —CF$_2$O— | 2-fluorophenyl | $CF_3$ | |
| 30 | $C_5H_{11}$ | — | 2,3-difluorophenyl | —CF$_2$O— | 2-fluorophenyl | $CF_3$ | |
| 31 | $CH_3$ | — | 2-fluorophenyl | —CF$_2$O— | 2,3-difluorophenyl | F | |
| 32 | $C_2H_5$ | — | 2-fluorophenyl | —CF$_2$O— | 2,3-difluorophenyl | F | |
| 33 | $C_3H_7$ | — | 2-fluorophenyl | —CF$_2$O— | 2,3-difluorophenyl | F | C 68 SmA(A) 84 SmA 112 N 145 I; Clp. = 128 Δε = 29 Δn = 0.107 |
| 34 | $C_4H_9$ | — | 2-fluorophenyl | —CF$_2$O— | 2,3-difluorophenyl | F | |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 35 | $C_5H_{11}$ | — | 3-F-phenylene | —CF$_2$O— | 3,5-diF-phenylene | F | |
| 36 | $CH_3$ | — | 3-F-phenylene | —CF$_2$O— | 3,5-diF-phenylene | $OCF_3$ | |
| 37 | $C_2H_5$ | — | 3-F-phenylene | —CF$_2$O— | 3,5-diF-phenylene | $OCF_3$ | |
| 38 | $C_3H_7$ | — | 3-F-phenylene | —CF$_2$O— | 3,5-diF-phenylene | $OCF_3$ | |
| 39 | $C_4H_9$ | — | 3-F-phenylene | —CF$_2$O— | 3,5-diF-phenylene | $OCF_3$ | |
| 40 | $C_5H_{11}$ | — | 3-F-phenylene | —CF$_2$O— | 3,5-diF-phenylene | $OCF_3$ | |
| 41 | $CH_3$ | — | 3-F-phenylene | —CF$_2$O— | 3,5-diF-phenylene | $CF_3$ | |
| 42 | $C_2H_5$ | — | 3-F-phenylene | —CF$_2$O— | 3,5-diF-phenylene | $CF_3$ | |

TABLE 1-continued

Compounds for Example 1.

| # | R$^{11}$ | A$^{11}$ | A$^{21}$ | Z$^{21}$ | A$^{22}$ | X$^{11}$ | Values |
|---|---|---|---|---|---|---|---|
| 43 | C$_3$H$_7$ | — | 3-F-phenylene | —CF$_2$O— | 3,5-diF-phenylene | CF$_3$ | |
| 44 | C$_4$H$_9$ | — | 3-F-phenylene | —CF$_2$O— | 3,5-diF-phenylene | CF$_3$ | |
| 45 | C$_5$H$_{11}$ | — | 3-F-phenylene | —CF$_2$O— | 3,5-diF-phenylene | CF$_3$ | |
| 46 | CH$_3$ | — | cyclohexylene | —CF$_2$O— | 3,5-diF-phenylene | F | |
| 47 | C$_2$H$_5$ | — | cyclohexylene | —CF$_2$O— | 3,5-diF-phenylene | F | |
| 48 | C$_3$H$_7$ | — | cyclohexylene | —CF$_2$O— | 3,5-diF-phenylene | F | C 88 SmB 175 N 207 I Clp. = 180 Δε = 24 Δn = 0.085 γ$_1$ = 813 |
| 49 | C$_4$H$_9$ | — | cyclohexylene | —CF$_2$O— | 3,5-diF-phenylene | F | |
| 50 | C$_5$H$_{11}$ | — | cyclohexylene | —CF$_2$O— | 3,5-diF-phenylene | F | |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 51 | $CH_3$ | — | cyclohexyl | —$CF_2O$— | 3,4-difluorophenyl | $OCF_3$ | |
| 52 | $C_2H_5$ | — | cyclohexyl | —$CF_2O$— | 3,4-difluorophenyl | $OCF_3$ | |
| 53 | $C_3H_7$ | — | cyclohexyl | —$CF_2O$— | 3,4-difluorophenyl | $OCF_3$ | |
| 54 | $C_4H_9$ | — | cyclohexyl | —$CF_2O$— | 3,4-difluorophenyl | $OCF_3$ | |
| 55 | $C_5H_{11}$ | — | cyclohexyl | —$CF_2O$— | 3,4-difluorophenyl | $OCF_3$ | |
| 56 | $CH_3$ | — | cyclohexyl | —$CF_2O$— | 3,4-difluorophenyl | $CF_3$ | |
| 57 | $C_2H_5$ | — | cyclohexyl | —$CF_2O$— | 3,4-difluorophenyl | $CF_3$ | |
| 58 | $C_3H_7$ | — | cyclohexyl | —$CF_2O$— | 3,4-difluorophenyl | $CF_3$ | |

TABLE 1-continued
Compounds for Example 1.
| # | $R^{11}$ | $A^{11}$ | $A^{21}$ | $Z^{21}$ | $A^{22}$ | $X^{11}$ | Values |
|---|---|---|---|---|---|---|---|
| 59 | $C_4H_9$ | — |  | —$CF_2O$— | 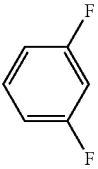 | $CF_3$ | |
| 60 | $C_5H_{11}$ | — |  | —$CF_2O$— | 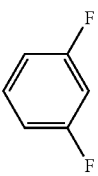 | $CF_3$ | |
| 61 | $CH_3$ | — | 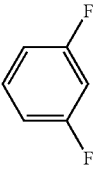 | — | 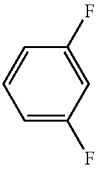 | F | |
| 62 | $C_2H_5$ | — | 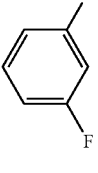 | — | 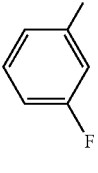 | F | |
| 63 | $C_3H_7$ | — | 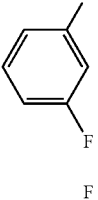 | — | 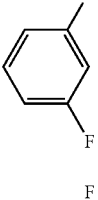 | F | C 103 N 148 I<br>Clp. = 126<br>Δε = 34<br>Δn = 0.124 |
| 64 | $C_4H_9$ | — | 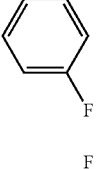 | — | 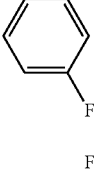 | F | |
| 65 | $C_5H_{11}$ | — | 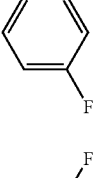 | — | 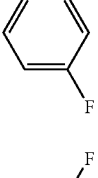 | F | |
| 66 | $CH_3$ | — | 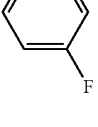 | — | 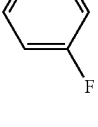 | $OCF_3$ | |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 67 | $C_2H_5$ | — | 3,5-difluorophenyl | — | 3,5-difluorophenyl | $OCF_3$ | |
| 68 | $C_3H_7$ | — | 3,5-difluorophenyl | — | 3,5-difluorophenyl | $OCF_3$ | |
| 69 | $C_4H_9$ | — | 3,5-difluorophenyl | — | 3,5-difluorophenyl | $OCF_3$ | |
| 70 | $C_5H_{11}$ | — | 3,5-difluorophenyl | — | 3,5-difluorophenyl | $OCF_3$ | |
| 71 | $CH_3$ | — | 3,5-difluorophenyl | — | 3,5-difluorophenyl | $CF_3$ | |
| 72 | $C_2H_5$ | — | 3,5-difluorophenyl | — | 3,5-difluorophenyl | $CF_3$ | |
| 73 | $C_3H_7$ | — | 3,5-difluorophenyl | — | 3,5-difluorophenyl | $CF_3$ | |
| 74 | $C_4H_9$ | — | 3,5-difluorophenyl | — | 3,5-difluorophenyl | $CF_3$ | |

TABLE 1-continued
Compounds for Example 1.
| # | $R^{11}$ | $A^{11}$ | $A^{21}$ | $Z^{21}$ | $A^{22}$ | $X^{11}$ | Values |
|---|---|---|---|---|---|---|---|
| 75 | $C_5H_{11}$ | — | 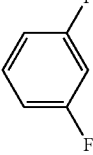 | — | 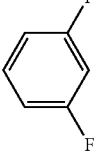 | $CF_3$ | |
| 76 | $CH_3$ | — |  | — | 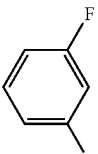 | F | |
| 77 | $C_2H_5$ | — |  | — | 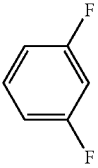 | F | |
| 78 | $C_3H_7$ | — |  | — | 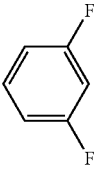 | F | C 132 SmB 161 N 211 I; Clp. = 173 $\Delta\epsilon = 22$ $\Delta n = 0.091$ |
| 79 | $C_4H_9$ | — |  | — | 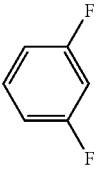 | F | |
| 80 | $C_5H_{11}$ | — |  | — | 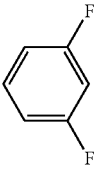 | F | |
| 81 | $CH_3$ | — |  | — | 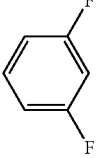 | $OCF_3$ | |
| 82 | $C_2H_5$ | — |  | — | 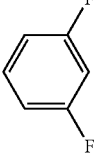 | $OCF_3$ | |

TABLE 1-continued
Compounds for Example 1.
| # | $R^{11}$ | $A^{11}$ | $A^{21}$ | $Z^{21}$ | $A^{22}$ | $X^{11}$ | Values |
|---|---|---|---|---|---|---|---|
| 83 | $C_3H_7$ | — |  | — | 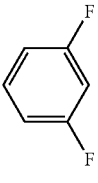 | $OCF_3$ | |
| 84 | $C_4H_9$ | — |  | — | 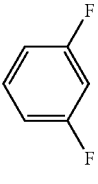 | $OCF_3$ | |
| 85 | $C_5H_{11}$ | — |  | — | 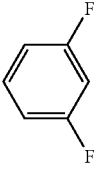 | $OCF_3$ | |
| 86 | $CH_3$ | — |  | — | 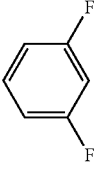 | $CF_3$ | |
| 87 | $C_2H_5$ | — |  | — | 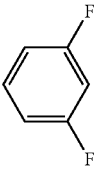 | $CF_3$ | |
| 88 | $C_3H_7$ | — |  | — | 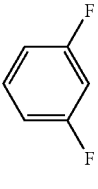 | $CF_3$ | |
| 89 | $C_4H_9$ | — |  | — | 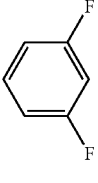 | $CF_3$ | |
| 90 | $C_5H_{11}$ | — |  | — | 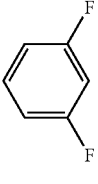 | $CF_3$ | |

TABLE 1-continued
Compounds for Example 1.
| # | $R^{11}$ | $A^{11}$ | $A^{21}$ | $Z^{21}$ | $A^{22}$ | $X^{11}$ | Values |
|---|---|---|---|---|---|---|---|
| 91 | $CH_3$ | — |  | — | 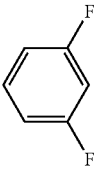 | F | |
| 92 | $C_2H_5$ | — |  | — | 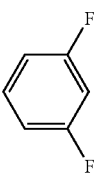 | F | |
| 93 | $C_3H_7$ | — |  | — | 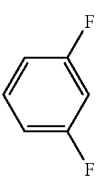 | F | C 101 SmA(A) 104 SmA 197 N 223 I<br>Clp. = 201<br>$\Delta\epsilon = 26$<br>$\Delta n = 0.150$ |
| 94 | $C_4H_9$ | — |  | — | 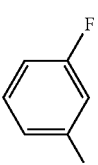 | F | |
| 95 | $C_5H_{11}$ | — |  | — | 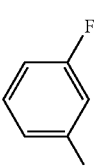 | F | |
| 96 | $CH_3$ | — |  | — | 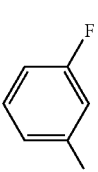 | $OCF_3$ | |
| 97 | $C_2H_5$ | — |  | — | 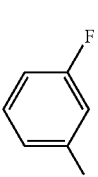 | $OCF_3$ | |
| 98 | $C_3H_7$ | — |  | — | 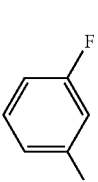 | $OCF_3$ | |

TABLE 1-continued
Compounds for Example 1.
| # | $R^{11}$ | $A^{11}$ | $A^{21}$ | $Z^{21}$ | $A^{22}$ | $X^{11}$ | Values |
|---|---|---|---|---|---|---|---|
| 99 | $C_4H_9$ | — |  | — | 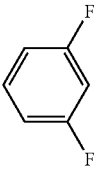 | $OCF_3$ | |
| 100 | $C_5H_{11}$ | — |  | — | 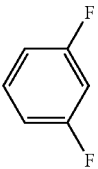 | $OCF_3$ | |
| 101 | $CH_3$ | — |  | — | 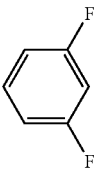 | $CF_3$ | |
| 102 | $C_2H_5$ | — |  | — | 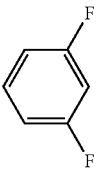 | $CF_3$ | |
| 103 | $C_3H_7$ | — |  | — | 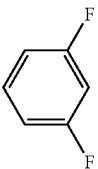 | $CF_3$ | |
| 104 | $C_4H_9$ | — |  | — | 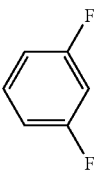 | $CF_3$ | |
| 105 | $C_5H_{11}$ | — |  | — | 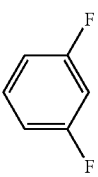 | $CF_3$ | |
| 106 | $CH_3$ |  | 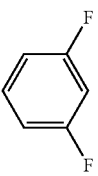 | —$CF_2O$— | 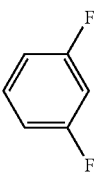 | F | |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 107 | $C_2H_5$ | cyclohexyl | 2,3-difluorophenyl | —CF$_2$O— | 3,5-difluorophenyl | F | |
| 108 | $C_3H_7$ | cyclohexyl | 2,3-difluorophenyl | —CF$_2$O— | 3,5-difluorophenyl | F | C 95 N 251 I<br>Clp. = 219<br>$\Delta\epsilon$ = 30<br>$\Delta n$ = 0.120 |
| 109 | $C_4H_9$ | cyclohexyl | 2,3-difluorophenyl | —CF$_2$O— | 3,5-difluorophenyl | F | |
| 110 | $C_5H_{11}$ | cyclohexyl | 2,3-difluorophenyl | —CF$_2$O— | 3,5-difluorophenyl | F | |
| 111 | $CH_3$ | cyclohexyl | — | — | 3,5-difluorophenyl | F | |
| 112 | $C_2H_5$ | cyclohexyl | — | — | 3,5-difluorophenyl | F | |
| 113 | $C_3H_7$ | cyclohexyl | — | — | 3,5-difluorophenyl | F | C 118 N 206 I<br>Clp. = 190<br>$\Delta\epsilon$ = 21<br>$\Delta n$ = 0.089<br>$\gamma_1$ = 1330 |
| 114 | $C_4H_9$ | cyclohexyl | — | — | 3,5-difluorophenyl | F | C 107 N 210 I<br>Clp. = 195<br>$\Delta\epsilon$ = 22<br>$\Delta n$ = 0.101<br>$\gamma_1$ = 1457 |

TABLE 1-continued

Compounds for Example 1.

| # | $R^{11}$ | $A^{11}$ | $A^{21}$ | $Z^{21}$ | $A^{22}$ | $X^{11}$ | Values |
|---|---|---|---|---|---|---|---|
| 115 | $C_5H_{11}$ |  | — | — |  | F | F |

EXAMPLE 2

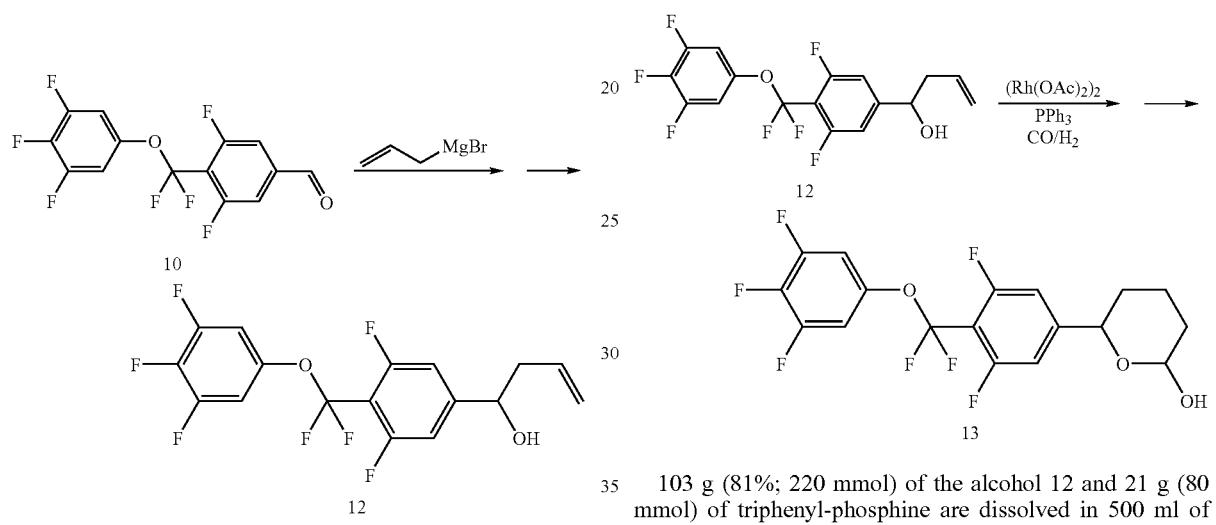

800 ml of a 1 M solution of allylmagnesium bromide in diethyl ether are added to a solution of 272 g (800 mmol) of the aldehyde 10 in 500 ml of THF under nitrogen at a temperature below 25° C. The batch is stirred overnight at RT, added to ice-water and subsequently extracted with methyl tertiary-butyl ether. The organic phase is washed with saturated NaCl solution, dried over sodium sulfate and evaporated. The resultant residue is passed over silica gel.

103 g (81%; 220 mmol) of the alcohol 12 and 21 g (80 mmol) of triphenyl-phosphine are dissolved in 500 ml of ethyl acetate, and 500 mg of rhodium acetate dimer are added. The hydroformylation is carried out at 25 bar of synthesis gas and 100° C. The reaction solution is evaporated and passed over silica gel.

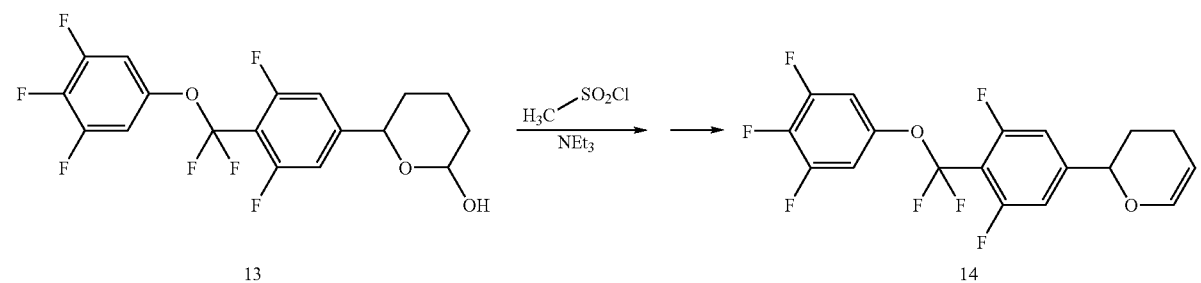

24.5 ml (320 mmol) of methanesulfonyl chloride are added to a solution of 100 g (240 mmol) of the lactol 13 and 101 ml (299 mmol) of triethylamine in 500 ml of dichloromethane at 0-5° C. under nitrogen. The batch is stirred overnight at room temperature. The batch is added to water and extracted with MTB ether. The organic phase is washed with saturated NaCl solution, dried over sodium sulfate and evaporated. The resultant residue is passed over silica gel.

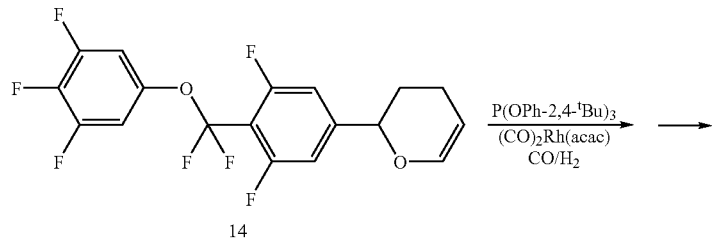

14

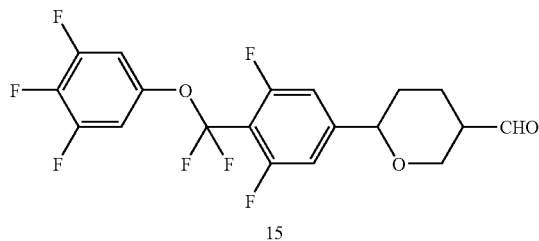

15

60 g (148 mmol) of the enol ether 14 are dissolved in 300 ml of toluene, and 9.8 g (15 mmol) of tris(2,4-di-tert-butylphenyl) phosphite and 390 mg (1.5 mmol) of dicarbonylrhodium(I) acetylacetonate are added. The hydroformylation is carried out at 100 bar of synthesis gas and 100° C. The solution is subsequently evaporated, and the residue is passed over silica gel, giving a cis/trans mixture of the aldehyde 15.

The signals of the aldehyde protons are at δ=9.69 ppm and δ=9.88 ppm.

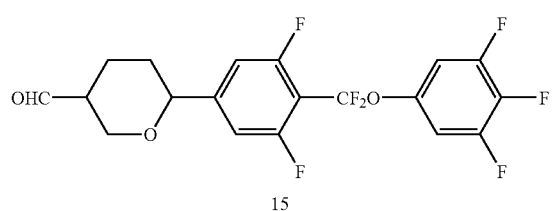

15

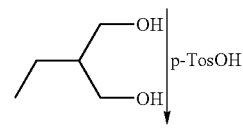

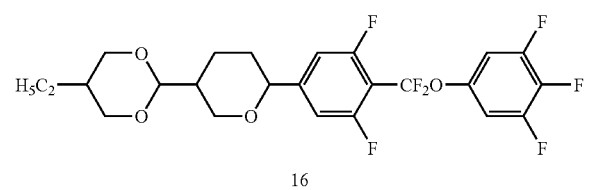

16

The aldehyde 15 is subsequently reacted with 2-ethyl-1,3-propanediol to give the dioxane 16. To this end, 44.5 g (110 mmol) of the aldehyde 15 and 11.2 g of the diol are dissolved in 250 ml of toluene, 400 mg of p-toluenesulfonic acid monohydrate are added, and the mixture is heated under reflux on a water separator until the aldehyde has reacted completely (TLC). The cooled batch is washed three times with sat. sodium hydrogencarbonate solution, evaporated and passed over silica gel (toluene/heptane 7:3; toluene; toluene/ethyl acetate 95:5). The product-containing fractions are evaporated, and the residue is recrystallised from ethanol at −20° C.

The following compounds are prepared analogously from a corresponding aldehyde together with a corresponding diol:

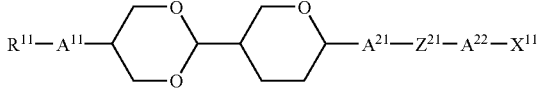

where $R^{12}$, $A^{11}$, $A^{21}$, $Z^{21}$ $A^{22}$ and $X^{11}$ denote, in particular, in accordance with Table 2:

TABLE 2
Compounds for Example 2.
| # | R$^{11}$ | A$^{11}$ | A$^{21}$ | Z$^{21}$ | A$^{22}$ | X$^{11}$ | Values |
|---|---|---|---|---|---|---|---|
| 1 | CH$_3$ | — | 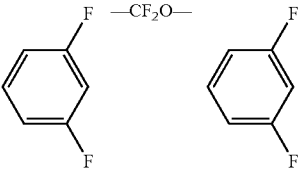 | —CF$_2$O— | 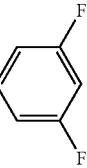 | F | |
| 2 | C$_2$H$_5$ | — | 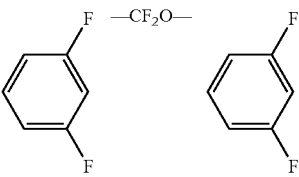 | —CF$_2$O— |  | F | C 88 N (87.9) I; Clp. = 69 Δε = 36 Δn = 0.088 γ$_1$ = 379 mPas |
| 3 | C$_3$H$_7$ | — | 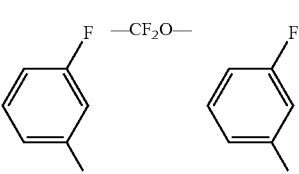 | —CF$_2$O— | 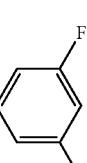 | F | C 95 N 112 I; Clp. = 85 Δε = 35 Δn = 0.097 γ$_1$ = 490 mPas |
| 4 | C$_4$H$_9$ | — | 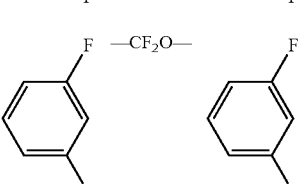 | —CF$_2$O— | 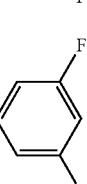 | F | |
| 5 | C$_5$H$_{11}$ | — | 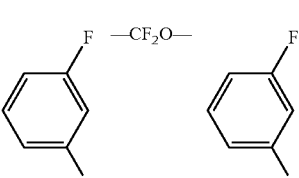 | —CF$_2$O— | 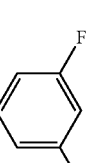 | F | |
| 6 | CH$_3$ | — | 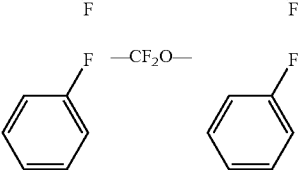 | —CF$_2$O— | 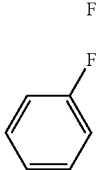 | OCF$_3$ | |
| 7 | C$_2$H$_5$ | — | 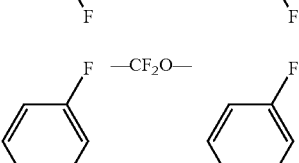 | —CF$_2$O— | 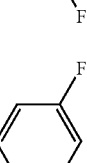 | OCF$_3$ | |
| 8 | C$_3$H$_7$ | — | 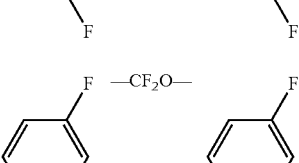 | —CF$_2$O— | 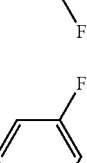 | OCF$_3$ | |

TABLE 2-continued
Compounds for Example 2.
| # | $R^{11}$ | $A^{11}$ | $A^{21}$ | $Z^{21}$ | $A^{22}$ | $X^{11}$ | Values |
|---|---|---|---|---|---|---|---|
| 9 | $C_4H_9$ | — | 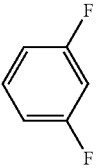 | —CF$_2$O— | 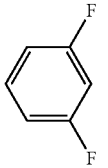 | OCF$_3$ | |
| 10 | $C_5H_{11}$ | — | 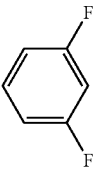 | —CF$_2$O— | 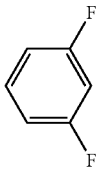 | OCF$_3$ | |
| 11 | $CH_3$ | — | 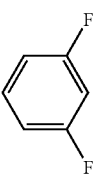 | —CF$_2$O— | 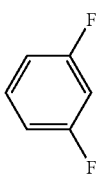 | CF$_3$ | |
| 12 | $C_2H_5$ | — | 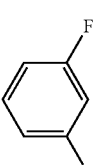 | —CF$_2$O— | 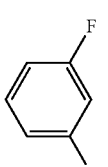 | CF$_3$ | |
| 13 | $C_3H_7$ | — | 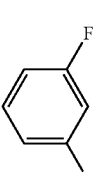 | —CF$_2$O— | 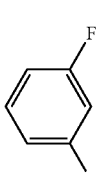 | CF$_3$ | |
| 14 | $C_4H_9$ | — | 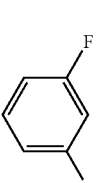 | —CF$_2$O— | 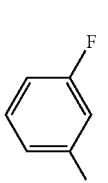 | CF$_3$ | |
| 15 | $C_5H_{11}$ | — | 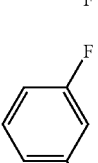 | —CF$_2$O— | 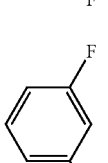 | CF$_3$ | |
| 16 | $CH_3$ |  | — | — | 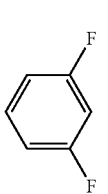 | F | |

TABLE 2-continued

Compounds for Example 2.

| # | $R^{11}$ | $A^{11}$ | $A^{21}$ | $Z^{21}$ | $A^{22}$ | $X^{11}$ | Values |
|---|---|---|---|---|---|---|---|
| 17 | $C_2H_5$ | cyclohexyl | — | — | difluorophenyl | F | |
| 18 | $C_3H_7$ | cyclohexyl | — | — | difluorophenyl | F | C 106 N 207 I; Clp. = 189 $\Delta\epsilon$ = 21 $\Delta n$ = 0.087 $\gamma_1$ = 1395 |
| 19 | $C_4H_9$ | cyclohexyl | — | — | difluorophenyl | F | C 91 SmH (63) N 203 I Clp. = 185 $\Delta\epsilon$ = 21 $\Delta n$ = 0.088 $\gamma_1$ = 1314 |
| 20 | $C_5H_{11}$ | cyclohexyl | — | — | difluorophenyl | F | |

EXAMPLE 3

The synthesis of 17 from the aldehyde 15 and the corresponding diol 2-(4-trans-propylcyclohexyl)-1,3-propanediol 9 also succeeds analogously to Example 2.

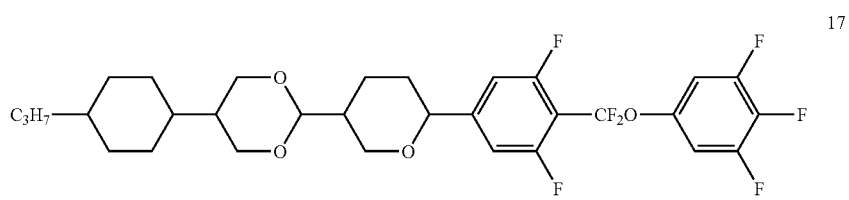

17

EXAMPLE 4

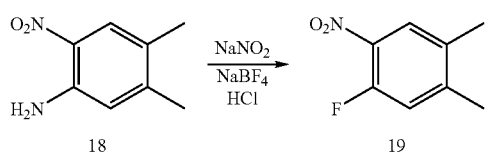

A solution of 6.9 g (10 mmol) of sodium nitrite in 12 ml of water is added dropwise at a temperature of 5-10° C. with vigorous stirring to a mixture of 16.6 g (100 mmol) of the aniline 18, 13 ml of conc. hydrochloric acid and 15.4 g (140 mmol) of sodium tetrafluoroborate in 40 ml of water. After 1 h at 25° C., the batch is filtered. The solid is washed with ice-water, methanol and MTB ether and dried under reduced pressure. The diazonium salt is subsequently subjected to careful thermal decomposition. The residue formed is extracted twice with MTB ether. The extracts are washed with 10% sodium hydroxide solution and saturated NaCl solution and dried over sodium sulfate. After evaporation, the residue is purified on silica gel.

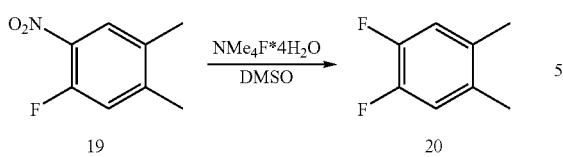

200 ml of DMSO and 18 g (110 mmol) of tetramethylammonium fluoride tetrahydrate are dried azeotropically using 400 ml of cyclohexane under nitrogen (6 h). 17 g (100 mmol) of the nitro compound 19 are subsequently added to the solvents at 80° C. The reaction is monitored by TLC. When the reaction is complete, the cooled batch is added to water and extracted with n-pentane. The organic phase is washed with saturated NaCl solution, dried over sodium sulfate and evaporated. The residue is purified on silica gel.

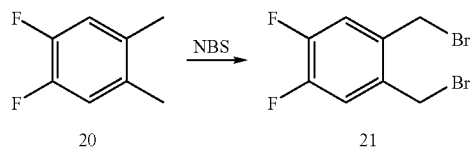

78 g (440 mmol) of N-bromosuccinimide and 1 g of azobisisobutyronitrile are added to a solution of 25 g (176 mmol) of the aromatic compound 20 in 250 ml of tetrachloromethane, and the mixture is warmed carefully until the reaction commences. After the reaction subsides, the batch is heated at the boil for 30 min. After cooling, the solid is separated off and washed with tetrachloromethane. The filtrate is evaporated, and the residue is purified on silica gel.

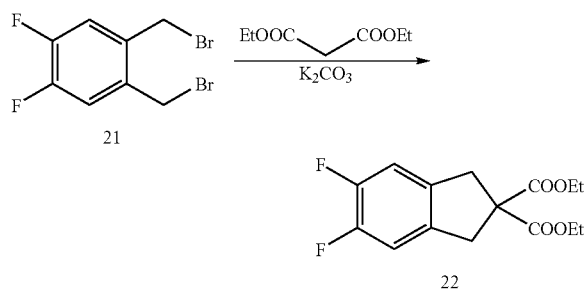

16.0 g (100 mmol) of diethyl malonate and 30 g (100 mmol) of the dibromide 21 are added to a suspension of 34.5 g (250 mmol) of potassium carbonate in 350 ml of ethyl methyl ketone, and the mixture is heated at the boil until the reaction is complete (TLC). The solid is separated off. The filtrate is evaporated, and the residue is purified on silica gel.

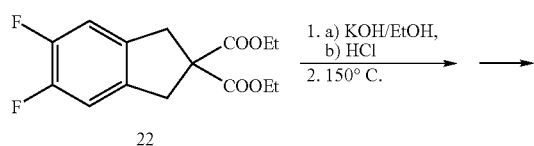

-continued

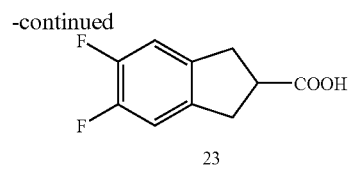

50 g (168 mmol) of the malonic ester derivative 22 are introduced into a solution of 22.4 g (400 mmol) of potassium hydroxide in 150 ml of ethanol and 50 ml of water, and the mixture is heated under reflux until the ester cleavage is complete (TLC). The alcohol is subsequently distilled off, the residue is acidified using semi-conc. hydrochloric acid and extracted with MTB ether. The organic phase is evaporated. The residue is carefully heated to 150° C. The reaction product is employed without further purification in the following step.

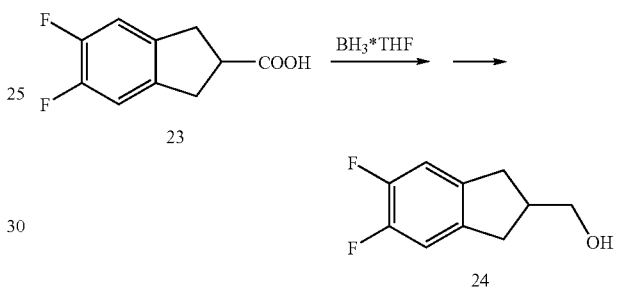

60 ml (60 mmol) of a 1 M solution of borane/tetrahydrofuran complex in THF are added to 10.3 g (52.0 mmol) of the acid 23 in 60 ml of dichloromethane at 0° C. under nitrogen. During the addition, the temperature of the reaction solution is kept below 5° C. The batch is subsequently warmed to RT and stirred overnight. 130 ml of 1 N hydrochloric acid are now carefully introduced into the reaction vessel. The aqueous phase is extracted twice with dichloromethane. The organic phase is dried and evaporated. The residue is purified on silica gel.

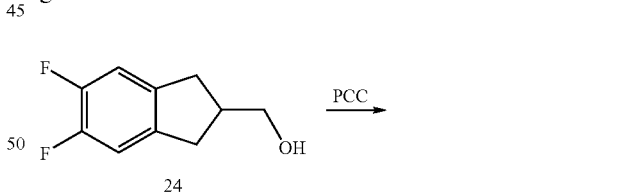

9.6 g (44.4 mmol) of pyridinium chlorochromate and 60 g of Celite® (J. T. Baker) are suspended in 50 ml of dichloromethane under nitrogen, and a solution of 6.8 g (36.7 mmol) of the alcohol 24 in 40 ml of dichloromethane is added. When the reaction is complete, the solid is separated off and washed with dichloromethane. The eluate is washed with 1 N sodium hydroxide solution and 2N hydrochloric acid and evaporated. The resultant residue is passed over silica gel.

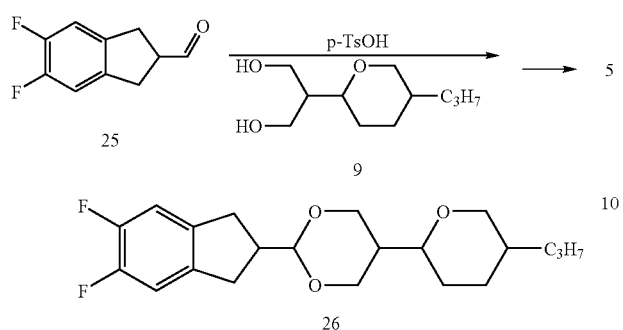

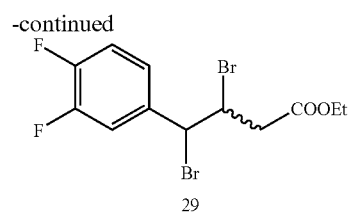

A solution of 5.1 ml (100 mmol) of bromine in 10 ml of dichloromethane is added to a solution of 27.6 g (100 mmol) of the unsaturated ester 28 in 75 ml of dichloromethane at 0-5° C. When the reaction is complete, the solvent is distilled off, and the residue is purified on silica gel.

15.8 g (78 mmol) of the diol 9 are dissolved in 100 ml of toluene with 14.2 g (78 mmol) of the aldehyde 26, 500 mg of p-toluenesulfonic acid monohydrate are added, and the mixture is heated to the boil on a water separator. The batch is subsequently passed over silica gel, and the eluate is evaporated. The resultant residue is purified by crystallisation from acetonitrile, acetone and heptane.

EXAMPLE 5

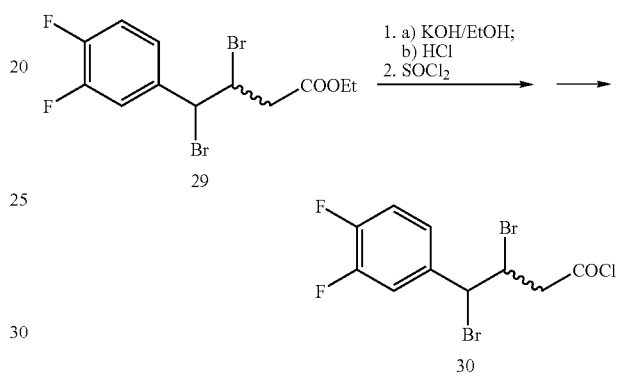

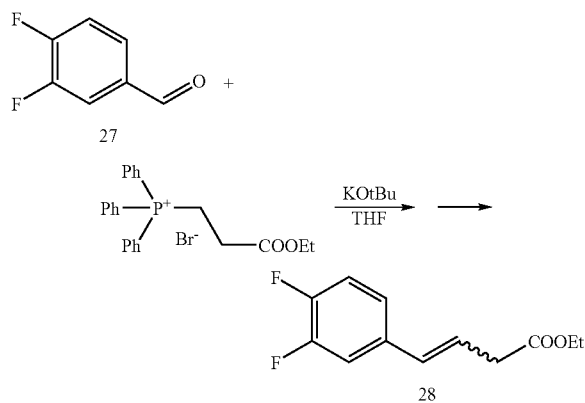

38.6 g (100 mmol) of the ester 29 are stirred for 5 h in ethanolic potassium hydroxide solution. The alcohol is subsequently distilled off, the residue is taken up in water, acidified using hydrochloric acid and extracted with MTB ether. The organic phase is dried over sodium sulfate and evaporated. 50 ml of thionyl chloride and one drop of dimethylformamide are added to the resultant residue, and the mixture is heated under reflux until the evolution of gas is complete. Excess thionyl chloride is distilled off. The residue is employed without further purification in the next step.

66.5 g (150 mmol) of the Wittig salt are suspended in 200 ml of THF under nitrogen, and a solution of 15.7 g (140 mmol) of potassium tert-butoxide in 75 ml of THF is added at 5-10° C. After one hour, 19.9 g (140 mmol) of the aldehyde 27, dissolved in 75 ml of THF, are added, during which the temperature does not exceed 8° C. The cooling is subsequently removed. After 20 h at RT, water is added to the batch. The aqueous phase is extracted with MTB ether. The organic phase is washed with saturated NaCl solution, dried over sodium sulfate and evaporated. The residue is purified over silica gel.

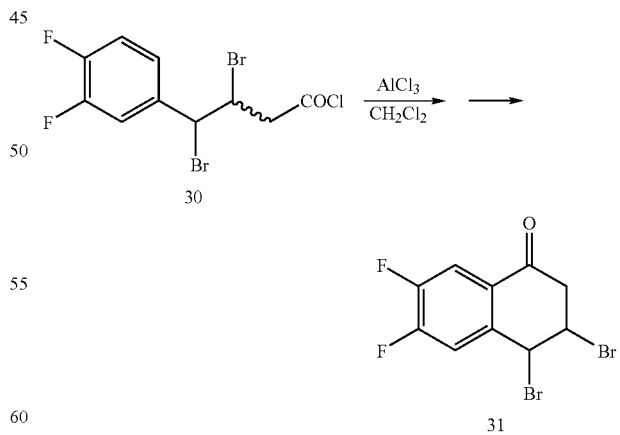

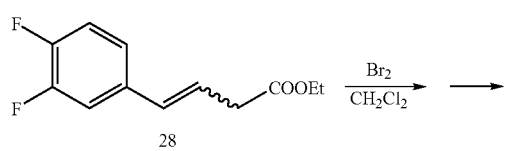

A solution of 37.0 g (about 105 mmol) of the crude acid chloride 30 in 120 ml of dichloromethane is added to a suspension of 16.4 g (119 mmol) of aluminium chloride in 80 ml of dichloromethane under nitrogen and at −20 to −15° C. After 4.5 h, the reaction is terminated by addition of ice, and the mixture is acidified using hydrochloric acid. The aqueous phase is extracted with methylene chloride. The organic phase is dried over sodium sulfate and evaporated. The residue is chromatographed on silica gel.

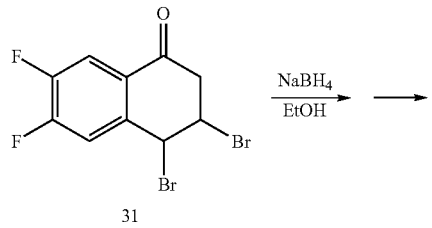

10.6 g (31.1 mmol) of the ketone 31 are dissolved in 150 ml of ethanol, and 1.2 g (32.5 mmol) of sodium borohydride are added in portions. When the reaction is complete (TLC), the batch is hydrolysed using water, the ethanol is removed under reduced pressure, the residue is taken up in water and extracted with toluene. After evaporation, the product is employed without further purification in the next step.

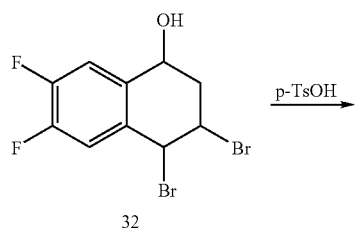

10.0 g of the crude diol 32 are dissolved in 200 ml of toluene, 1 g of p-toluenesulfonic acid is added, and the mixture is heated under reflux until the separation of water is complete. The batch is subsequently evaporated. The resultant residue is purified on silica gel.

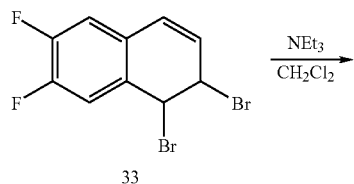

-continued

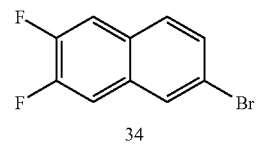

10.4 ml (75 mmol) of triethylamine are added to a solution of 16.2 g (50 mmol) of the dibromide 33 in 75 ml of dichloromethane, and the mixture is stirred at RT for 4 h. The batch is subsequently washed with water and saturated NaCl solution and dried over sodium sulfate. The residue obtained after the evaporation is purified on silica gel.

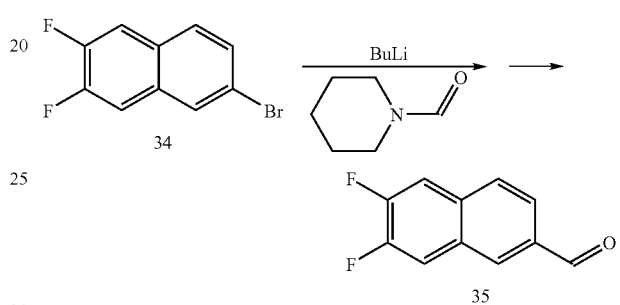

38.8 ml (95.0 mmol) of a 2.5M n-butyllithium solution in hexane are added to a solution of 22.4 g (92.0 mmol) of the aromatic compound 34 in 200 ml of diethyl ether at −75° C., and the mixture is stirred for 1 h. 13.4 ml (120 mmol) of formylpiperidine, dissolved in 15 ml of diethyl ether, are subsequently added at below −55° C. After a further hour, the batch is warmed to RT, water is added, and the mixture is acidified. Extraction, drying and evaporation are followed by purification on silica gel.

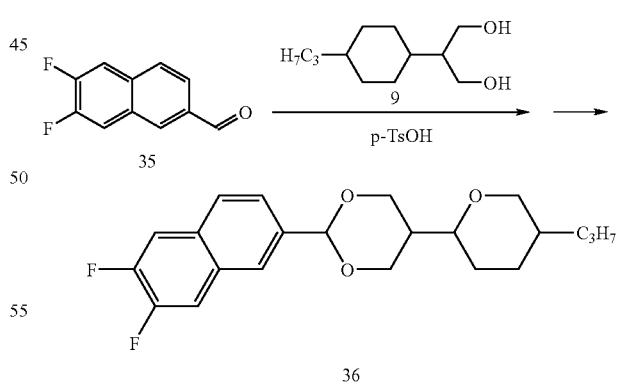

7.9 g (39 mmol) of the diol 9 are dissolved in 100 ml of toluene with 7.5 g (39 mmol) of the aldehyde 35, 500 mg of p-toluenesulfonic acid mono-hydrate are added, and the mixture is heated to the boil on a water separator. The batch is subsequently passed over silica gel, and the eluate is evaporated. The resultant residue is purified by crystallisation from acetonitrile, acetone and heptane. 36: Δ∈=20; Δn=0.148.

EXAMPLE 6

The naphthalene derivative 38 is prepared analogously to Example 5 starting from trifluorobenzaldehyde 37.

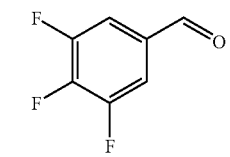

38: Δε = 30; Δn = 0.140.

EXAMPLE 7

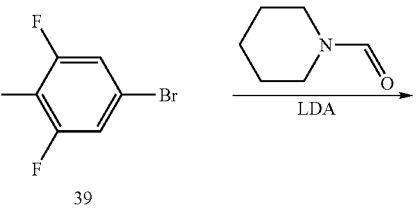

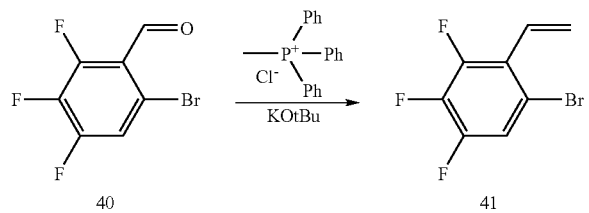

60.0 ml (120 mmol) of a 2.0M lithium diisopropylamide solution in THF/ethylbenzene are added to a solution of 22.4 g (106 mmol) of trifluoro-bromobenzene 39 in 200 ml of THF at −75° C., and the mixture is stirred for 1 h. 13.4 ml (120 mmol) of formylpiperidine, dissolved in 15 ml of THF, are subsequently added at below −55° C. After a further hour, the batch is warmed to RT, water is added, and the mixture is acidified. Extraction, drying and evaporation are followed by purification on silica gel.

31.5 g (94.5 mmol) of the Wittig salt are suspended in 130 ml of THF under nitrogen, and a solution of 9.9 g (88.2 mmol) of potassium tert-butoxide in 50 ml of THF is added at 5-10° C. After one hour, 33.5 g (140 mmol) of the aldehyde 40, dissolved in 50 ml of THF, are added, during which the temperature does not exceed 8° C. The cooling is subsequently removed. After 20 h at RT, water is added to the batch. The aqueous phase is extracted with MTB ether. The organic phase is washed with saturated NaCl solution, dried over sodium sulfate and evaporated. The residue is purified over silica gel.

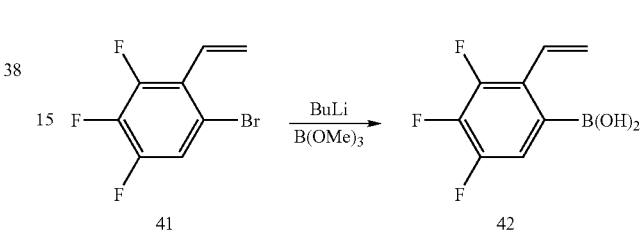

61.3 ml (150 mmol) of a 2.5M n-butyllithium solution in hexane are added to a solution of 35.6 g (150 mmol) of the aromatic compound 41 in 250 ml of diethyl ether at −75° C., and the mixture is stirred for 1 h. 15.6 g (150 mmol) of trimethyl borate, dissolved in 15 ml of diethyl ether, are subsequently added at below −55° C. After a further hour, the batch is warmed to RT, water is added, and the mixture is acidified. After extraction with MTB ether, the organic phase is dried, evaporated and washed by stirring with n-heptane at 0° C. The acid is employed without further purification in the following step.

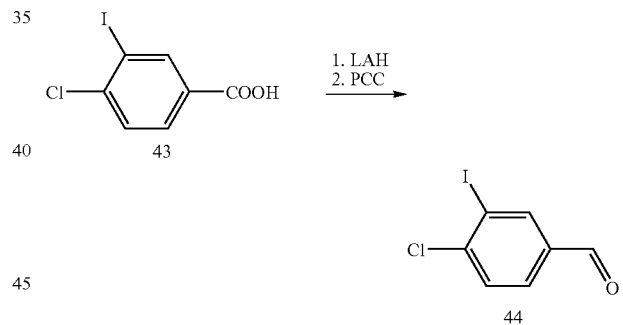

A solution of 28.2 g (100 mmol) of the acid 43 in 100 ml of THF is added to a suspension of 3.0 g (80 mmol) of lithium aluminium hydride in 50 ml of THF, and the mixture is heated at the boil for 2 h. The cooled batch is carefully hydrolysed using a THF/water mixture, and a solution of 22.9 g of sodium carbonate decahydrate in 20 ml of water at 80° C. is subsequently added. After the mixture has been stirred for 30 min, the solid is separated off. The organic phase is dried and evaporated. The residue is reacted further without further purification.

45 g of pyridinium chlorochromate (PCC) are added to a suspension of 120 g of Celite® (J. T. Baker) in 450 ml of dichloromethane under nitrogen. A solution of the residue in 75 ml of dichloromethane is subsequently added to the suspension. The batch is stirred overnight at RT. The Celite® is separated off and washed with dichloromethane. The organic phase is evaporated, and the resultant residue is passed over silica gel.

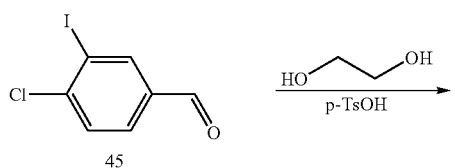

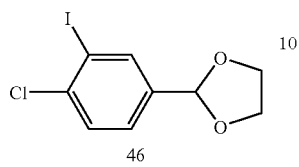

26.6 g (100 mmol) of the aldehyde 45 are dissolved in 150 ml of toluene, 8.0 g (129 mmol) of ethylene glycol and 500 mg of p-toluenesulfonic acid monohydrate are added, and the mixture is heated at the boil on a water separator. The batch is subsequently washed with saturated sodium hydrogencarbonate solution and evaporated. The residue is purified on silica gel.

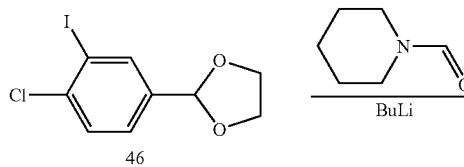

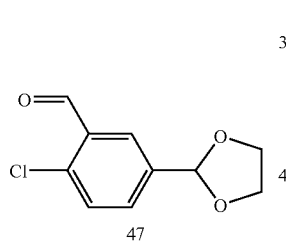

38.8 ml (95.0 mmol) of a 2.5M butyllithium solution in hexane are added to a solution of 28.6 g (92.0 mmol) of the aromatic compound 46 in 200 ml of diethyl ether at −75° C., and the mixture is stirred for 1 h. 13.4 ml (120 mmol) of formylpiperidine, dissolved in 15 ml of diethyl ether, are subsequently added at below −55° C. After a further hour, the batch is warmed to RT, water is added, and the mixture is acidified. Extraction, drying and evaporation are followed by purification on silica gel.

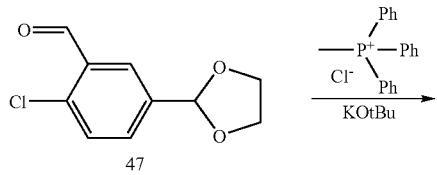

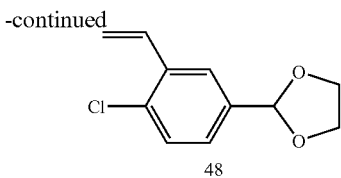

37.5 g (112.5 mmol) of the Wittig salt are suspended in 150 ml of THF under nitrogen, and a solution of 11.8 g (105 mmol) of potassium tert-butoxide in 60 ml of THF is added at 5-10° C. After one hour, 29.8 g (140 mmol) of the aldehyde 47, dissolved in 60 ml of THF, are added, during which the temperature does not exceed 8° C. The cooling is subsequently removed. After 20 h at RT, water is added to the batch. The aqueous phase is extracted with MTB ether. The organic phase is washed with saturated NaCl solution, dried over sodium sulfate and evaporated. The residue is purified over silica gel.

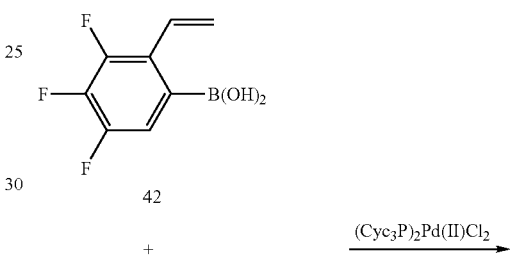

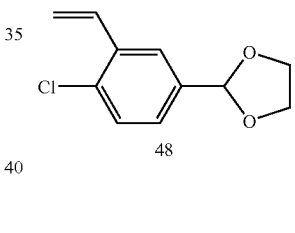

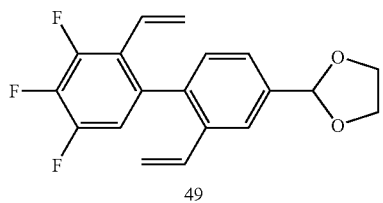

28.5 g (75 mmol) of disodium tetraborate decahydrate are introduced into 35 ml of water under nitrogen, and 1.25 g (1.6 mmol) of bis(tricyclohexyl-phosphine)palladium(II) chloride and 0.1 ml of hydrazinium hydroxide are added. After 5 min, 85 ml of THF, 17.3 g (82 mmol) of the chloride 48 and 18.2 g (90 mmol) of the boronic acid 42 are added. The batch is heated under reflux for 24 h. Water is added to the cooled batch, and the mixture is extracted three times with MTB ether. The organic phase is washed with saturated NaCl solution, dried over sodium sulfate and evaporated. The resultant residue is purified on silica gel.

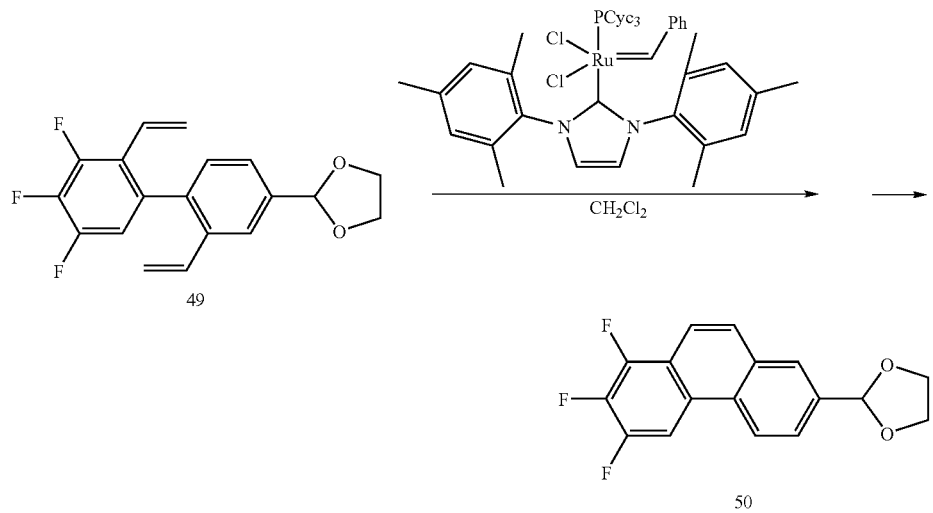

20.0 g (60 mmol) of the biphenyl 49 are dissolved in 500 ml of dichloromethane, and 2.5 g (3 mmol) of the ruthenium catalyst are added. The batch is held at 40° C. until the evolution of gas is complete. The solvent is subsequently removed. The resultant residue is purified on silica gel.

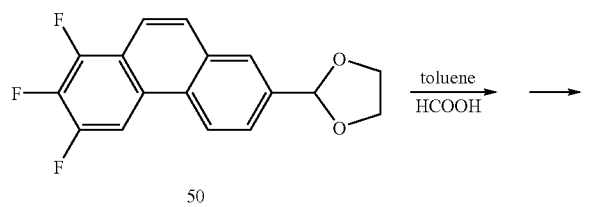

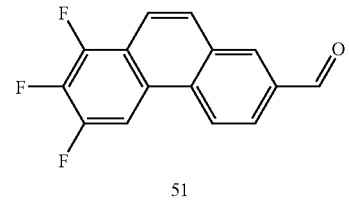

50 ml of formic acid are added to a solution of 20.0 g (65.7 mmol) of the ketal 50 in 150 ml of toluene under nitrogen, and the mixture is stirred overnight at RT. The batch is subsequently added to 300 ml of water, and the mixture is diluted with 300 ml of heptane. The organic phase is separated off, washed with saturated sodium hydrogencarbonate solution and evaporated. The residue is purified on silica gel.

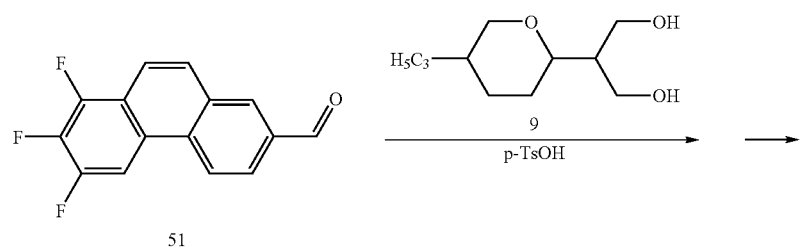

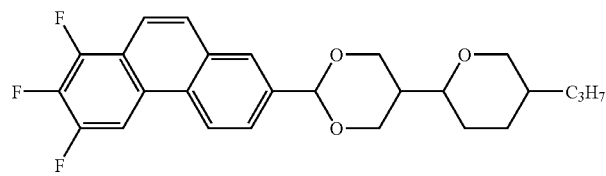

10.0 g (49 mmol) of the diol 9 are dissolved in 100 ml of toluene with 12.7 g (49 mmol) of the aldehyde 51, 500 mg of p-toluenesulfonic acid monohydrate are added, and the mixture is heated at the boil on a water separator. The batch is subsequently passed over silica gel, and the eluate is evaporated. The resultant residue is purified by crystallisation from acetonitrile, acetone and heptane. 52: Δ∈=29; Δn=0.189.

The invention claimed is:

1. Compounds of the general formula I $$R^1\text{---}[A^1\text{---}Z^1]_m\text{---}B^1\text{---}[Z^2\text{---}A^2]_n\text{---}R^2 \quad I$$

in which $B^1$ denotes

[structures shown]

or

[structures shown], $R^1$, $R^2$ denote H, halogen, CN, SCN, NCS, $SF_5$, a linear or branched, optionally chiral alkyl radical having 1 to 15 C atoms which is unsubstituted, monosubstituted by CN or $CF_3$ or mono- or polysubstituted by halogen and in which one or more $CH_2$ groups may each be replaced, independently of one another, by —O—, —S—, —CO—, —CO—O—, —O—CO—, —CH=CH—, —CH=CF—, —CF=CF—, —C≡C—, —CH$_2$O— or —CF$_2$O— in such a way that heteroatoms are not linked directly to one another and asymmetrical groups may be present in both orientations, $A^1$, $A^2$ each, independently of one another, identically or differently, denote a) trans-1,4-cyclohexylene, in which, in addition, one or more non-adjacent $CH_2$ groups may be replaced by —O— and/or —S—, b) 1,4-phenylene, in which one or two CH groups may be replaced by N and in which one or more H atoms may be replaced by Br, Cl, F, CN, methyl, methoxy or a mono- or polyfluorinated methyl or methoxy group, c) a radical from the group 1,4-bicyclo[2.2.2]octylene, piperidine-1,4-diyl, cyclobutane-1,3-diyl, spiro[3.3]heptane-2,6-diyl,

[structures shown], in which hydrogen atoms may be mono- or polysubstituted by F, CN, SCN, $SF_5$, $CH_2F$, $CHF_2$ or $CF_3$, $OCH_2F$, $OCHF_2$ or $OCF_3$, one or more double bonds may be replaced by single bonds, M, $M^1$ or $M^2$ denotes —O—, —S—, —$CH_2$—, —CHY— or —$CYY^1$—, and Y and $Y^1$ denote Cl, F, CN, $OCF_3$ or $CF_3$, or d) 1,4-cyclohexenylene, $Z^1$, $Z^2$ each, independently of one another, identically or differently, denote a single bond, —$CH_2O$—, —CO—O—, —$CF_2O$—, —$CH_2CH_2CF_2O$—, —$CF_2CF_2$—, —$CH_2CF_2$—, —$CH_2CH_2$—, —CH=CH—, CH=CF—, —CF=CF— or —C≡C—, where asymmetrical bridges may be oriented to both sides, and n, m, independently of one another, denote 0, 1, 2 or 3, with the proviso that if m=0, n=1 and at the same time $A^2$ denotes a phenylene as in b), then $Z^2$, in the stated orientation, denotes —$CH_2O$—, —CO—O—, —$CF_2O$—, —$CH_2CH_2CF_2O$—, —$CF_2CF_2$—, —$CH_2CF_2$—, —$CF_2H_2$—, —$CH_2CH_2$—, —CH=CH—, —CH=CF—, —CF=CH— or —CF=CF—.

2. Compounds according to claim 1, wherein n denotes 1, 2 or 3, and at least one of the groups $Z^2$ denotes —$CF_2O$—, —CO—O—, —CF=CF—, —$CH_2O$— or —$CF_2CF_2$—.

3. Compounds according to claim 1, of the sub-formula IA

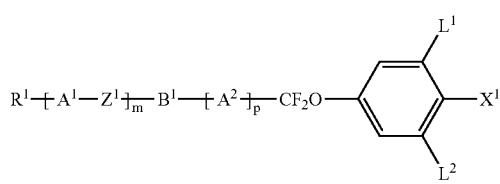

IA in which
p denotes 0, 1 or 2,
m+p denotes 0, 1 or 2,
$L^1$ $L^2$, independently of one another, denote H, F, Cl, CN or $CF_3$, and
$X^1$ denotes H, halogen, CN, SCN, NCS, $SF_5$, a linear or branched alkyl
radical having 1 to 8 C atoms which is monosubstituted by CN or $CF_3$ or at least monosubstituted by halogen and in which one or more $CH_2$ groups may each, independently of one another, be replaced by —O—, —CF=CF— or —C≡C— in such a way that heteroatoms are not linked directly to one another.

4. Compounds according to claim 3, of sub-formula IB

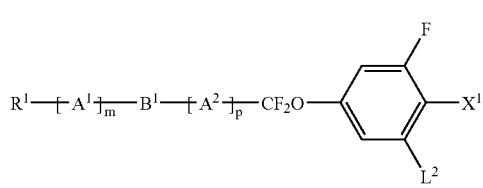

IB in which
$L^2$ denotes H or F,
$X^1$ denotes F or $OCF_3$, $CF_3$, CN, SCN, NCS, $SF_5$,
$A^1$ denotes a 1,4-cyclohexanediyl,
$A^2$ denotes a group of the formula

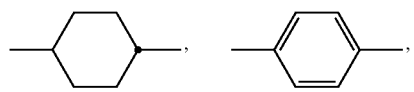

-continued

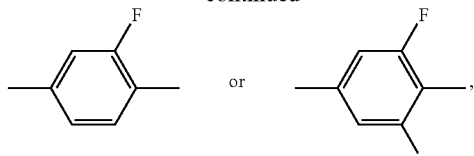

m denotes 0 or 1,
p denotes 0 or 1, and
m+p denotes 0 or 1.

5. Compounds according to claim 1, wherein
$R^1$ denotes a linear alkyl or alkoxy radical having 1 to 12 C atoms or a linear alkenyl or alkenyloxy radical having 2 to 12 C atoms.

6. Compounds according to claim 1, wherein $B^1$ denotes

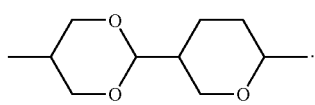

7. Compounds according to claim 1, wherein $B^1$ denotes

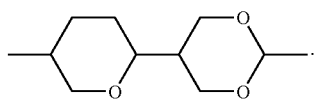

8. Compounds according to claim 1, wherein
$Z^1$ and $Z^2$, independently of one another, denote —$CF_2O$—, —$CF_2CF_2$—, —CF=CF— or a single bond.

9. Liquid-crystalline medium at least two liquid-crystalline components, wherein one component is at least one pyrandioxane derivative according to claim 1.

10. Liquid-crystal display element, containing a liquid-crystalline medium according to claim 9.

11. Electro-optical display element, containing a dielectric, which dielectric is a liquid-crystalline medium according to claim 9.

* * * * *